United States Patent
Mortensen et al.

(10) Patent No.: US 11,653,689 B2
(45) Date of Patent: May 23, 2023

(54) **PROBIOTIC *BIFIDOBACTERIUM BREVE* STRAIN AND COMPOSITIONS COMPRISING SAID STRAIN**

(71) Applicant: Chr. Hansen A/S, Hoersholm (DK)

(72) Inventors: Brynjulf Mortensen, Hoersholm (DK); Anders Damholt, Hoersholm (DK); Anja Wellejus, Hoersholm (DK); Vibeke Westphal Stennicke, Hoersholm (DK); Johan E. T. Van Hycklama Vlieg, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 73 days.

(21) Appl. No.: 17/051,653

(22) PCT Filed: May 1, 2019

(86) PCT No.: PCT/EP2019/061161
§ 371 (c)(1),
(2) Date: Oct. 29, 2020

(87) PCT Pub. No.: WO2019/211341
PCT Pub. Date: Nov. 7, 2019

(65) Prior Publication Data
US 2021/0153535 A1    May 27, 2021

(30) Foreign Application Priority Data
May 1, 2018  (EP) ...................................... 8170250

(51) Int. Cl.
*A23L 33/135*   (2016.01)
*A61P 1/00*     (2006.01)
(Continued)

(52) U.S. Cl.
CPC .......... *A23L 33/135* (2016.08); *A61K 35/745* (2013.01); *A61K 45/06* (2013.01); *A61P 1/00* (2018.01)

(58) Field of Classification Search
CPC ...... A61K 31/00; A61K 35/745; A61K 45/06; A23L 33/135; A61P 1/00; A61P 1/04; C12R 2001/01; C12N 1/205
See application file for complete search history.

(56) References Cited

U.S. PATENT DOCUMENTS

2014/0072543 A1*  3/2014  Mogna ................... A61K 35/74
                                                  435/252.9

FOREIGN PATENT DOCUMENTS

WO    WO-2013/034974 A1    3/2013

OTHER PUBLICATIONS

Bjarnason et al., "Mechanisms of Damage to the Gastrointestinal Tract From Nonsteroidal Anti-Inflammatory Drugs", Gastroenterology, vol. 154, pp. 500-514 (Feb. 2018).
(Continued)

*Primary Examiner* — Jana A Hines
(74) *Attorney, Agent, or Firm* — Foley & Lardner LLP

(57) ABSTRACT

The present invention relates to *Bifidobacterium breve* deposited as DSM 32356 and compositions comprising said strain. The composition may further comprise at least one other bacterial strain and/or at least one compound which may be an NSAID such as acetylsalicylic acid (aspirin). In a presently preferred embodiment the invention relates to *Bifidobacterium breve* deposited as DSM 32356 for use in the support of the defense against intestinal tissue damage such as intestinal mucosal breaks or lesions e.g. in connection with NSAID administration such as in connection with administration of acetylsalicylic acid (aspirin). The invention further provides a method of supporting the defense
(Continued)

Figure 1:
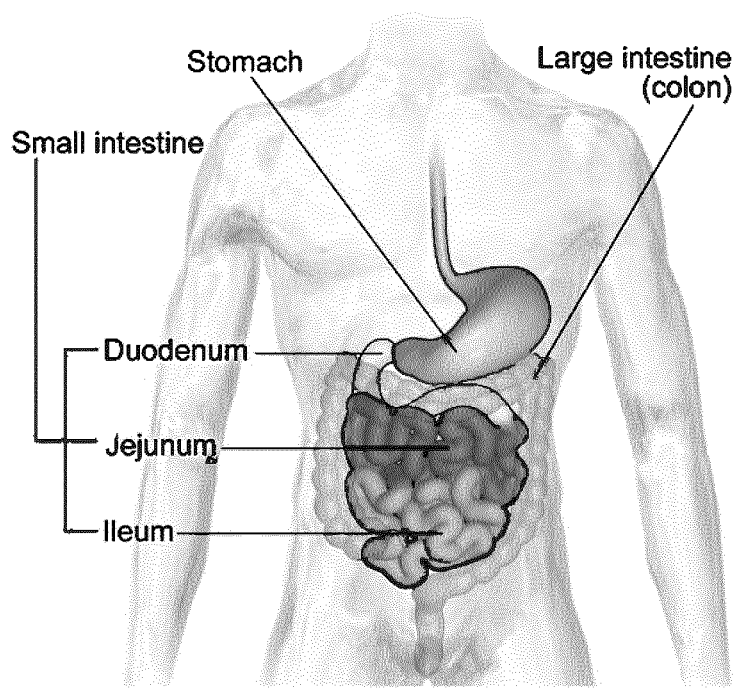

against intestinal tissue damage, the method comprising administering the *Bifidobacterium breve* strain deposited as DSM 32356 to a subject in need thereof, e.g. to a subject in need of NSAID treatment.

19 Claims, 23 Drawing Sheets

(51) Int. Cl.
    *A61K 35/745*     (2015.01)
    *A61K 45/06*     (2006.01)

(56) References Cited

OTHER PUBLICATIONS

Doneanu et al., "UPLC/MS Monitoring of Water-Soluble Vitamin Bs in Cell Culture Media in Minutes", Waters Application note, 720004042en, pp. 1-7(2011).

Endo et al., "Efficacy of *Lactobacillus casei* treatment on small bowel injury in chronic low-dose aspirin users: A pilot randomized controlled study," J Gastroenterol (2011) vol. 46, pp. 894-905 (Published online May 2011).

FAO/WHO "Health and Nutritional Properties of Probiotics in Food including Powder Milk with Live Lactic Acid Bacteria," Report of a Joint FAO/WHO Expert Consultation on Evaluation of Health and Nutritional Properties of Probiotics in Food Including Powder Milk with Live Lactic Acid Bacteria, Amerian Córdoba Park Hotel; Córdoba, Argentina (Oct. 1-4, 2001).

Gotteland et al., "Effect of Lactobacillus ingestion on the gastrointestinal mucosal barrier alterations induced by indomethacin in humans," Aliment Pharmacol Ther. vol. 15, pp. 11-17 (2001).

Gralnek et al., "Development of a capsule endoscopy scoring index for small bowel mucosal inflammatory change," Aliment Pharmacol Ther. vol. 27, pp. 146-154 (2008).

Le Faounder et al.,"LC-MS/MS method for rapid and concomitant quantification of pro-inflammatory and pro-resolving polyunsaturated fatty acid metabolites", J. Chromatogr. B, vol. 932, pp. 123-133 (2013).

Montalto et al., "Clinical trial: the effects of a probiotic mixture on non-steroidal anti-inflammatory drug enteropathy—a randomized, double-blind, cross-over, placebo-controlled study," Aliment Phamacol Ther. vol. 32, pp. 209-214 (2010).

Nielsen et al., "Identification and assembly of genomes and genetic elements in complex metagenomic samples without using reference genomes", Nat. Biotechnol. vol. 32, No. 8, pp. 822-828 (plus "Online Methods") (Aug. 2014) (Published online Jul. 2014).

Suzuki et al., "Yogurt Containing *Lactobacillus gasseri* Mitigates Aspirin-Induced Small Bowel Injuries: A Prospective, Randomized, Double-Blind, Placebo-Controlled Trial," Digestion, (2017) vol. 95, pp. 49-54 (Published online Jan. 2017).

Syer et al., "NSAID enteropathy and bacteria: a complicated relationship," J Gastroenterol (2015) vol. 50, pp. 387-393 (Published online Jan. 2015).

Wallace, J. L., "Mechanisms, prevention and clinical implications of nonsteroidal anti-inflammatory drug-enteropathy", World J Gastroenterol. vol. 19, No. 12, pp. 1861-1876 (Mar. 2013).

Zankari et al., "Identification of acquired antimicrobial resistance genes," J. Antimicrob. Chemother., vol. 67, pp. 2640-2644 (2012).

\* cited by examiner

Figure 2
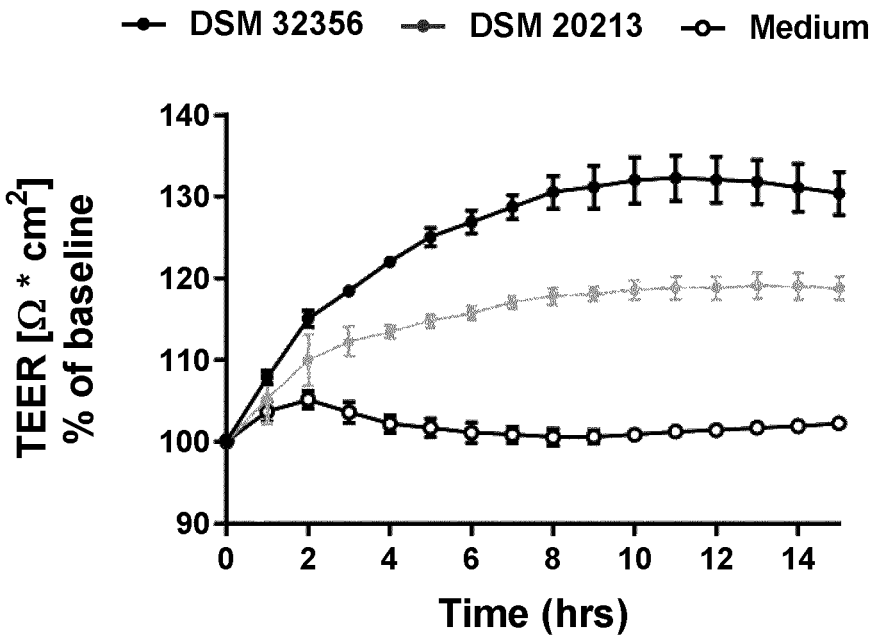
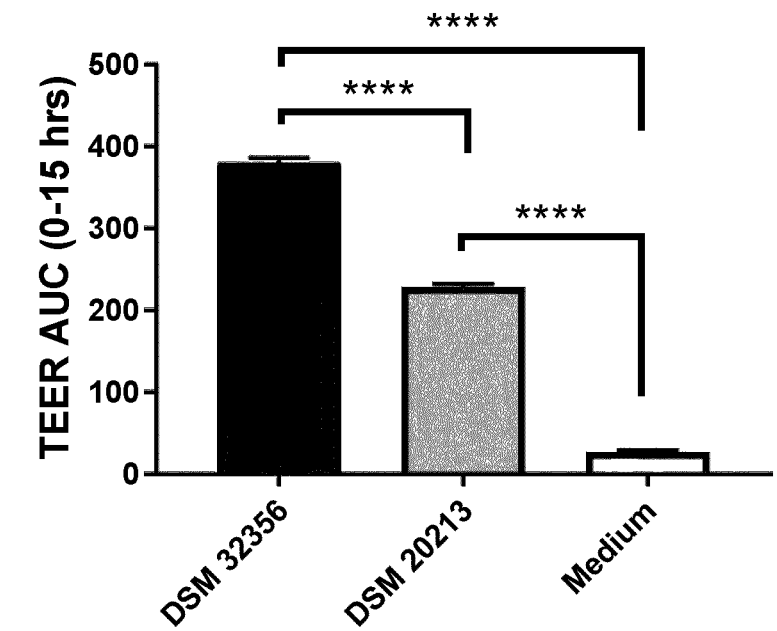

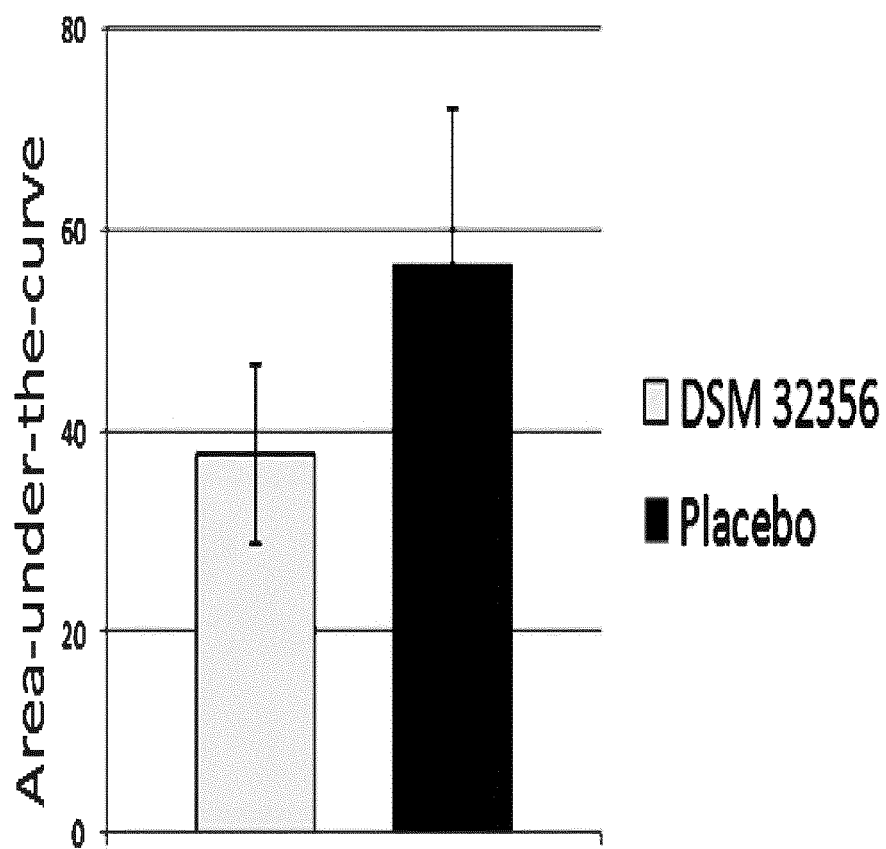

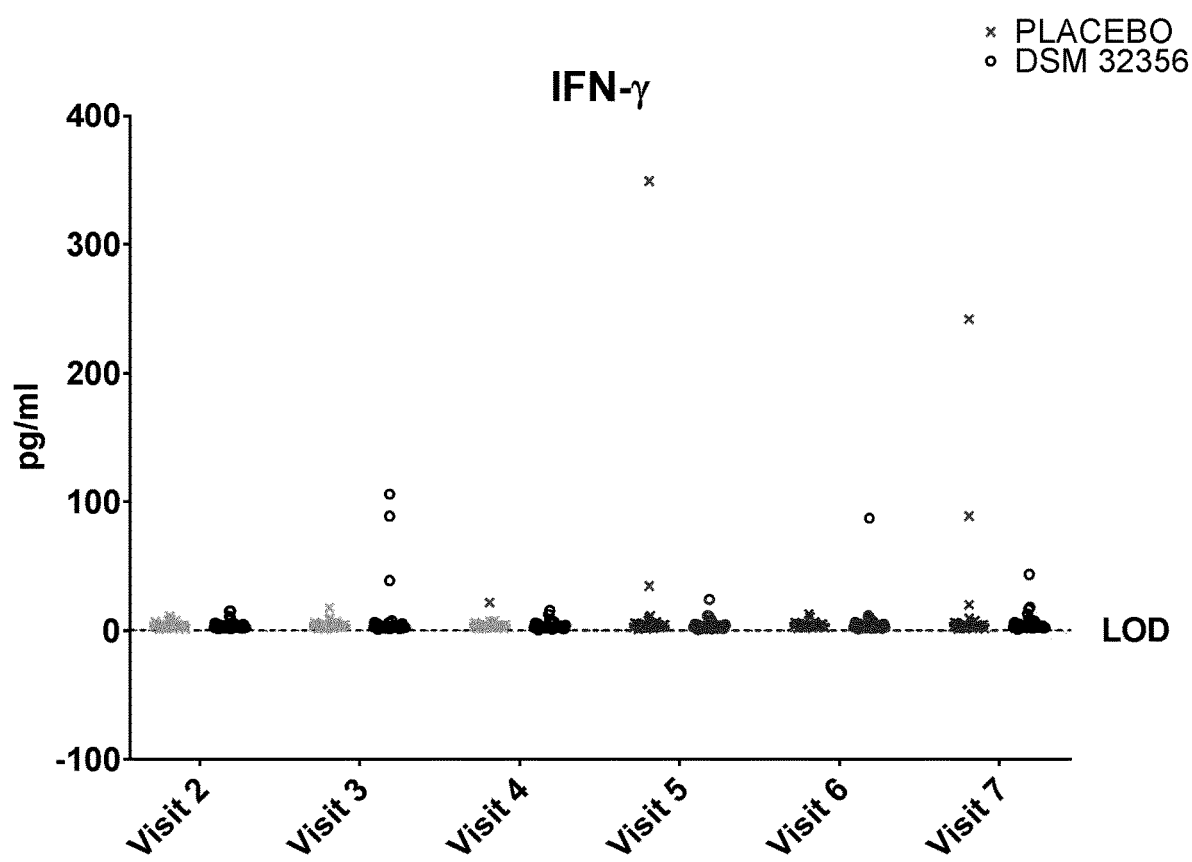

PROBIOTIC *BIFIDOBACTERIUM BREVE* STRAIN AND COMPOSITIONS COMPRISING SAID STRAIN

CROSS-REFERENCE TO RELATED APPLICATIONS

The present application is the U.S. National Stage of International Application PCT/EP2019/061161, filed May 1, 2019, and claims priority to European Patent Application No. 18170250.7, filed May 1, 2018.

FIELD OF THE INVENTION

The present invention relates to the *Bifidobacterium breve* strain deposited as DSM 32356 and compositions comprising said strain. In a presently preferred embodiment the invention relates to the *Bifidobacterium breve* strain deposited as DSM 32356 for use in the support of the defense against intestinal tissue damage in a subject in need thereof, e.g. during NSAID administration.

BACKGROUND OF THE INVENTION

Non-Steroidal Anti-Inflammatory Drugs (NSAIDs) are commonly used worldwide, both as prescription-only medicines and as "over-the-counter" preparations. They are often used in short-term treatments of many common pain-related conditions, including headaches and menstrual pain, and for long-term therapies of chronic inflammatory diseases such as osteoarthritis, rheumatoid arthritis, ankylosing spondylitis, and gout.

Chronic use of low-dose NSAIDS commonly defined as 75-325 mg daily is also recommended and prescribed for its cardiovascular-protecting properties. NSAIDs, such as acetylsalicylic acid (aspirin), has been shown to be helpful when used daily to lower the risk of heart attack, clot-related strokes and other blood flow problems in patients who have cardiovascular disease or who have already had a heart attack or stroke.

Furthermore, increasing evidence suggest that NSAIDs may be valuable for the prevention of cancer and neurodegenerative diseases and for the treatment of other inflammatory conditions.

Due to NSAIDs' wide range of indications and therapeutic properties, they are some of the most used pharmaceuticals in the world. In 2010, NSAIDs were regularly used by about 30 million of US adults. It is estimated that over one-third of the US adult population (including 80% of those with known cardiovascular disease) use low dose NSAIDs regularly.

However, low dose use of NSAIDS, such as acetylsalicylic acid (aspirin), is associated with gastrointestinal (GI) injury, and the degree of damage depends on dose, duration of treatment, concomitant medication and patient risk profiles. Accordingly, acetylsalicylic acid (aspirin) has emerged as one of the most prominent causes of peptic ulcer bleeding in developed countries and is associated with a 2- to 4-fold increased risk of upper GI bleeding and is increasing with concomitant medication use. Generally, patients taking NSAIDs experience a relative risk of upper GI bleeding and perforations of up to 4.7 compared with non-users. Strategies to prevent upper GI complications associated with NSAID use include among others proton-pump inhibitors (PIPs) and synthetic prostaglandin.

FIG. 1 shows an overview of the gastrointestinal tract, i.e. the stomach, the small intestine consisting of duodenum, jejunum and ileum, and the large intestine (colon).

Live bacteria formulated as probiotics may offer an alternative to prevent or at least decrease negative side effects of NSAIDS such as acetylsalicylic acid (aspirin). Gotteland et al., 2001 (Gotteland M, Cruchet S, Verbeke S. Effect of *Lactobacillus* ingestion on the gastrointestinal mucosal barrier alterations induced by indomethacin in humans. Aliment Pharmacol Ther. 2001; 15: 11-7) concluded that the regular ingestion of live *Lactobacillus rhamnosus* GG (LGG) may have a protective effect on the integrity of the gastric mucosal barrier against indo-methacin-induced injury but had no effect at intestinal level.

According to Wallace, 2013 (Wallace, J L, Mechanisms, prevention and clinical implications of nonsteroidal anti-inflammatory drug-enteropathy, World J Gastroenterol. 2013, Mar. 28; 19(12):1861-1876), the prevalence and clinical significance of NSAID-enteropathy continues to be greatly underrecognized. NSAID-induced enteropathy and bleeding occur more frequently than NSAID-induced gastropathy. Significant small intestinal damage and bleeding can be observed in about 70% of chronic NSAID users and in the majority of patients the injury is sub-clinical.

Unlike the case for NSAID gastropathy, there are no proven-effective preventative therapies for NSAID-induced enteropathy, and the pathogenesis is poorly understood. It occurs with greater frequency than the damage caused by these drugs in the upper gastrointestinal tract but is much more difficult to diagnose and treat.

Although the pathogenesis of NSAID enteropathy remains incompletely understood, it is clear that bacteria, bile, and the enterohepatic circulation of NSAIDs are all important factors. Inhibitors of gastric acid secretion significantly aggravate NSAID enteropathy, and this effect is due to significant changes in the intestinal microbiome (Syer, S. D., Blackler, R. W., Martin, R., de Palma, G., Rossi, L., Verdu, E., Bercik, P., Surette M. G., Aucouturier, A., Langella P., Wallace, J. L., NSAID enteropathy and bacteria: a complicated relationship, J Gastroenterol (2015), 50:387-393. doi 10.1007s00535-014-1032-1).

With improved means of detection, such as video capsule endoscopy, physicians are becoming more aware that the small intestinal damage caused by NSAIDs is much more common and much more serious than previously recognized.

Several studies have demonstrated beneficial effects of probiotics in experimental models of NSAID enteropathy. There have also been human studies which have demonstrated preventative effects of a single probiotic (*L. casei*) (Endo H, Higurashi T, Hosono K, et al. Efficacy of *Lactobacillus casei* treatment on small bowel injury in chronic low-dose aspirin users: A pilot randomized controlled study. J Gastroenterol. 2011; 46(7):894-905. doi:10.1007/s00535-011-0410-1) or of a cocktail of probiotics (Montalto M., Gallo A, Curigliano V, D'Onofrio F, Santoro L. Covino M., Dalvai S, Gasbarini A. and Gasbarrini G. Clinical trial: the effects of a probiotic mixture on non-steroidal anti-inflammatory drug enteropathy—a randomized, double-blind, cross-over, placebo-controlled study. Aliment Phamacol Ther 2010; 32: 209-214) against NSAID-induced small intestinal injury.

Montalto et al., 2010, tested the cocktail VSL #3 which consisted of four strains of Lactobacilli (*L. casei, L. plantarum, L. acidophilus, L. bulgaricus*), three strains of Bifidobacteria (*B. longum, B. breve* and *B. infantis*), and one strain of *Streptococcus salivaris* subspecies *thermophilus*). Treatment with VSL #3 before and during indomethacin therapy was found to significantly reduce faecal calprotectin (FCC) in healthy subjects with respect to placebo against NSAID-induced small intestinal injury. Capsule endoscopy was not performed in this study.

Endo et al., 2011 performed a clinical trial where twenty-five patients, including 13 in the *L. casei* group and 12 in the control group, underwent the full analysis of the small intestine (CE score) using wireless capsule endoscopy. Significant decreases in the number of mucosal breaks and the CE score were observed at the 3-month evaluation in the *L. casei* group as compared with the results in the control group.

US 2014/072543 (Mogna Giovanni) entitled "Composition comprising probiotic bacteria capable of restoring the barrier effect of the stomach which is lost during pharmacological treatment of gastric hyperacidity" claims a pharmaceutical or food composition or a supplement comprising at least one bacterial strain belonging to the species: *L. acidophilus, L. crispatus, L. gasseri, L. delbrueckii, L. salivarius, L. casei, L. paracasei, L. plantarum, L. rhamnosus, L. reuteri, L. brevis, L. buchneri, L. fermentum, L. lactis, L. pentosus, B. adolescentis, B. angulatum, B. bifidum, B. breve, B. catenulatum, B. infantis, B. lactis, B. longum, B. pseudocatenulatum* and *S. thermophilus*, which is capable of colonizing the stomach at a pH value comprised from 4.5 to 5 and of producing bacteriocins and/or metabolites and/or hydrogen peroxide, the pharmaceutical food composition or supplement being in a form suitable for administration of the at least one bacterial strain to the stomach of a subject.

No experimental data are provided in the application.

WO2013/034974 (Mogna et al.) entitled "Composition comprising N-acetylcysteine and/or microencapsulated gastroprotected lysozyme in association with probiotic bacteria capable of restoring the stomach's own barrier effect which is lost during the pharmaceutical treatment of gastric hyperacidity" claims a pharmaceutical or dietary composition or a supplement or a medical device for use in the treatment of subjects who are taking drugs to reduce or treat gastric hyperacidity which comprises or, alternatively, consists of at least one strain of bacteria belonging to one or more of the species chosen from the group comprising or, alternatively, consisting of: *L acidophilus, L. crispatus, L. gasseri, L. delbrueckii, L. delbr.* subsp. *delbrueckii, L. salivarius, L. casei, L. paracasei, L. plantarum, L. rhamnosus, L. reuteri, L. brevis, L. buchneri, L. fermentum, L. lactis, L. pentosus, B. adolescentis, B. angulation, B, bifidum, B. breve, B. catenulatum, B. infantis, B. lactis, B. longum, B. pseudocatenulatum* and *S. thermophilus* in association with N-acetylcysteine and/or lysozyme; said strain being capable of colonizing the stomach at a pH value comprised between 4.0 and 5.5 and of producing bacteriocins and/or metabolites and/or oxygenated water.

This application includes the results of a pilot study including 40 individuals in total. On the basis of this study the application concludes that the administration of an association of specific strains of *L. rhamnosus* LR06, *L. pentosus* LPS01, *L. plantarum* LP01, and *L. delbrueckii* LDD01, including also an efficacious quantity of N-acetylcysteine is capable of restoring a protective barrier against harmful bacteria, especially at stomach level. More recently Suzuki et al., 2017, (Suzuki T, Masui A, Nakamura J, et al. Yogurt Containing *Lactobacillus* gasseri Mitigates Aspirin-Induced Small Bowel Injuries: A Prospective, Randomized, Double-Blind, Placebo-Controlled Trial. Digestion. 2017; 95(1):49-54. doi:10.1159/000452361) reported a trial where 64 users of acetylsalicylic acid (aspirin) who had received acetylsalicylic acid (aspirin) for more than 1 month were enrolled. The patients received a yogurt containing *L. gasseri* or placebo twice daily for 6 weeks. Small bowel injuries were evaluated by capsule endoscopy before and after consuming the yogurt. The effect of *L. gasseri* on patient symptoms was also assessed using the Frequency Scale for the Symptoms of Gastroesophageal Reflux Disease (FSSG) and Gastrointestinal Symptom Rating Scale (GSRS) questionnaires before and after 6 weeks of treatment. In contrast with the placebo group, the *L. gasseri* group had significantly fewer small bowel mucosal breaks and reddened lesions after 6 weeks. The FSSG and GSRS scores were also significantly improved in the *L. gasseri* group but not in the placebo group.

Syer et al., 2015 demonstrated in an animal model that administration of *Bifidobacterium adolescentis* once daily for 5 days prior to initiation of twice daily naproxen administration resulted in a substantial reduction of intestinal ulceration. However, not all *Bifidobacterium* species were found effective for this application. For example, *Bifidobacterium longum* subsp. *Longum* JCM 1217 was ineffective in the same model.

Thus, a need still exists for identifying probiotic bacteria which can be useful in the support of the defense against intestinal tissue damage e.g. during NSAID administration.

SUMMARY OF THE INVENTION

The present invention relates to the *Bifidobacterium breve* strain deposited as DSM 32356. This strain has been found in a MIC test to be sensitive to all relevant antibiotics. Consistent herewith, no antibiotic resistance genes were identified when analysed as described in Example 1. Further, the strain was tested for cytotoxicity by the Vero cell assay and found to be non-cytotoxic.

Based upon the in vitro results provided in Example 1 the *Bifidobacterium breve* strain deposited as DSM 32356 is considered safe.

Example 2 provides the results of a transepithelial electrical resistance (TEER) assay. The results indicate that the strain increases the barrier integrity.

Aspirin has been acknowledged to introduce serious clinically relevant side-effects, such as erosions, ulcers and bleeding of the stomach and small intestine. Besides inhibiting the cyclooxygenase enzymes that results in decreased levels of mucosal prostaglandins, administration of aspirin also disrupts phospholipid layers, present both in mucus and epithelial cells surface bilayer, and uncouples oxidative phosphorylation. A combination of these processes decreases intestinal permeability, triggers inflammatory pathways and ultimately leads to apoptosis, mucosal erosions and ulcers (Bjarnasson et al. (2018) Gastroenterology, 154, 500-514.

Acute administration of aspirin induces significant increase in both gastroduodenal and small intestinal permeability in healthy subjects. The mechanism behind this is not completely elucidated, however, experimental in vitro studies suggest that aspirin decreases the expression of the tight junction protein Zonula Occludens-1 (ZO-1) which is considered one of the key markers for cell-to-cell contact and barrier integrity (Montalto, M., Maggiano, N., Ricci, R., Curigliano, V., Santoro, L., Di Nicuolo, F., Vecchio, F. M., Gasbarrine, A., Gasbarrini, G. (2004) Digestion, 69(4), 225-228). This was supported by recent data, showing how aspirin induces decreased transepithelial electrical resistance (TEER) as well as increases flux of fluorescein isothiocyanate-conjugated dextran across a Caco-2 cell layer, strongly suggesting increased permeability. Furthermore, the authors also discovered that ZO-1 expression was decreased in addition to an increase in the formation of reactive oxygen species (ROS) and oxidative stress-induced modifications in the ZO-1 protein (Fukui, A., Naito, Y., Handa, O., Kugai, M., Tsuji, T., Yoriki, H., Qin, Y., Adachi, S., Higashimura, Y., Mizushima, K., Kannada, K., Katada, K., Uchiyama, K., Ishikawa, T., Takagi, T., Yagi, N., Kokura, S. & Yoshikawa, T. (2012) Am J Physiol Gastrointest Liver Physiol 303, G927-G936).

The Caco-2 cell monolayer represents a well-established cell line, derived from human colon adenocarcinoma, which is commonly used as an intestinal permeability model.

Based upon the in vitro results provided in Example 2 where it is demonstrated that the *Bifidobacterium breve* strain deposited as DSM 32356 increases the electrical resistance across Caco-2 cell monolayer, measured by transepithelial electrical resistance, TEER, the strain is considered potentially useful in the support of the defense against intestinal tissue damage in a subject in need of NSAID treatment such as acetylsalicylic acid (aspirin).

Acetylsalicylic acid (aspirin) administration—even in low dosages—has been shown to introduce mucosal inflammation and injury of the small bowel (Endo, H., Sakai, E., Kato, T., Umezawa, S., Higurashi, T., Ohkubo, H. & Nakajima (2015) J Gastroenterol, 50, 378-386).

Modulation of the inflammatory status of the gastrointestinal tract is possible by dosing bacteria that will accordingly activate immune cells to secrete cytokines. For example, Foligne and co-workers (Foligne, B., Nutten, S., Grangette, C., Dennin, V., Goudercourt, D., Poirot, S., Dewulf, J., Brassart, D., Mercenier, A. & Pot, B. (2007) World J Gastroenterol, 13(2), 236-243) found a significant association between bacteria-mediated in vivo protection against experimental colitis and cytokine profile induced by the bacteria in vitro, in particular the IL-10 and interleukin 12 (IL-10/IL-12) ratio. The authors showed how in vivo protection against trinitrobenzene sulfonate (TNBS)-induced colitis in mice was mediated by bacterial strains with a capacity to induce high levels of the "anti"-inflammatory cytokine IL-10 and low levels of "pro"-inflammatory cytokine IL-12 in vitro. In contrast, strains inducing a low IL-10/IL-12 ratio were not capable of attenuating inflammatory colitis.

Thus, in vitro modulation of human inflammatory cells is a useful tool to predict induction of a pro- or anti-inflammatory gut environment induced by bacteria.

Example 3 shows that the *Bifidobacterium breve* strain deposited as DSM 32356 increases the IL-10/IL-12 ratio indicating anti-inflammatory properties. Accordingly, the strain could be useful against aspirin-induced small intestinal inflammation.

Example 4 provides the results of a large clinical trial where healthy volunteers were challenged with daily intake of 300 mg acetylsalicylic acid (aspirin) for 6 weeks to induce intestinal damage captured and quantified by the capsule endoscopy method. Subjects were also randomised to probiotic or placebo treatment on top of acetylsalicylic acid (aspirin) intake. The main endpoints of this trial clearly showed a significant protective effect on the acetylsalicylic acid-induced intestinal damage in the active probiotic arm compared to the placebo arm as measured by the Lewis score (Gralnek I M, Defranchis R, Seidman E, Leighton J A, Legnani P, Lewis B S. Development of a capsule endoscopy scoring index for small bowel mucosal inflammatory change. Aliment Pharmacol Ther. 2008; 27(2):146-154. doi: 10.1111/j.1365-2036.2007.03556.x).

Example 5 provides the results of the serum concentrations of PGE2 and TXB2 from study subjects in the placebo group versus the subjects dosed with DSM 32356 and shows that the strain does not affect the COX inhibition induced by aspirin. This suggests that the protective actions of DSM 32356 do not interfere with the specific cardiovascular properties of acetylsalicylic acid (aspirin).

Example 6 provides a systemic cytokine profiling from blood samples taken 1 day after the last dose. No significant differences between the placebo and the active group was found indicating no systemic effect of DSM 32356.

Example 7 shows that the relative abundance of *Bifidobacterium breve* increases during intervention with DSM 32356 demonstrating study product compliance. Further fecal biota composition was investigated and intervention with *Bifidobacterium breve* DSM 32356 did not appear to change fecal microbiota diversity significantly.

Example 8 provides the results of a co-incubation experiment of DSM 32356 with acetylsalicylic acid and shows that DSM 32356 does not seem to degrade acetylsalicylic acid (aspirin).

In accordance herewith, the present invention relates to *Bifidobacterium breve* deposited as DSM 32356 for use in the support of the defense against intestinal tissue damage in a subject in need thereof.

DETAILED DISCLOSURE OF THE INVENTION

Unless defined otherwise, all technical and scientific terms used herein have the same meaning as commonly understood by persons skilled in the art. Although any methods and materials equivalent or similar to those described herein can be used in the practice of the present disclosure, typical methods and materials are described. All methods described herein can be performed in any suitable order unless otherwise indicated herein or otherwise clearly contradicted by context.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The present invention provides an isolated *Bifidobacterium breve* strain deposited as DSM 32356 which is sensitive to gentamycin, streptomycin, tetracycline, erythromycin, clindamycin, chloramphenicol, ampicillin, and vancomycin in a MIC test when tested as described in Example 1, has no antibiotic resistance genes when analysed as described in Example 1, and was found to be non-cytotoxic when tested for cytotoxicity by the Vero cell assay as described in Example 1.

The *Bifidobacterium breve* strain deposited as DSM 32356 is further capable of (i) increasing the electrical resistance across Caco-2 cell monolayer, measured by transepithelial electrical resistance, TEER, by more than 20% after 10 hours treatment when tested as outlined in Example 2, where the *Bifidobacterium breve* strain deposited as DSM 32356 is compared with *Bifidobacterium breve* strain deposited as DSM 20213; (ii) inducing secretion of greater than 200 pg/ml of IL-10 when co-incubated with human monocyte-derived dendritic cells and (iii) inducing an increase of the IL-10/IL-12 ratio in DSM 32356 stimulated monocyte-derived dendritic cells compared to unstimulated monocyte-derived dendritic cells when tested as outlined in Example 3.

Finally, the *Bifidobacterium breve* strain deposited as DSM 32356 has been found to protect the intestinal tissue against damage such as mucosal breaks or lesions in a clinical study in healthy adults who are taking NSAID, e.g. acetylsalicylic acid. The results provided in Example 4 suggest that daily intake of 5 $10^{10}$ colony forming units (CFU) 20 *Bifidobacterium breve* deposited as DSM 32356 may reduce the risk of ulcers in healthy adults who are taking NSAID, e.g. acetylsalicylic acid, on a daily basis.

In the context of this invention, the term "probiotic component" refers to a culture of live or freeze-dried microorganisms, dead microorganisms, fragments of microorganisms and extracts or supernatants of microorganisms which, when applied to man or animal, beneficially affects the host (FAO/WHO (2001) Health and Nutritional Properties of Probiotics in Food including Powder Milk with Live Lactic Acid Bacteria. Report of a Joint FAO/WHO Expert Consultation on Evaluation of Health and Nutritional Properties of Probiotics in Food Including Powder Milk with Live Lactic Acid Bacteria).

The present invention provides *Bifidobacterium breve* deposited according to the Budapest Treaty on the International Recognition of the Deposit of Microorganisms for the Purposes of Patent Procedure with the Deutsche Sammlung von Mikroorganismen and Zellkulturen, Inhoffenstr. 7B, D-38124 Braunschweig on Aug. 9, 2016 under the accession number DSM 32356.

The invention relates to use of *Bifidobacterium breve* deposited as DSM 32356 as a probiotic.

The present invention further provides compositions comprising said strain.

A bacterial "strain" as used herein refers to a bacterium which remains genetically unchanged when grown or multiplied.

In a further aspect, the invention provides the *Bifidobacterium breve* strain deposited as DSM 32356 for use in the support of the defense against intestinal tissue damage in a subject in need thereof.

In the present context, the term "intestinal tissue damage" includes one or more red spots, erosions, lesions or mucosal breaks or areas with villous edema which may proceed to more severe damage such as stenosis or necrosis.

In the present context the term "mucosal break or lesion" is used synonymously with the term "ulcer" as this is the definition of ulcer which has been used in the present trial.

A presently preferred embodiment of the present invention relates to *Bifidobacterium breve* deposited as DSM 32356 for use during NSAID administration, such as during administration of acetylsalicylic acid (aspirin). Evidently, the *Bifidobacterium breve* deposited as DSM 32356 can also be used for recovery or reversal of intestinal tissue damage after NSAID administration.

Thus, the *Bifidobacterium breve* deposited as DSM 32356 may be useful during and after NSAID administration in connection with pain-related conditions, including headaches and menstrual pain, and in particular during long-term therapies of chronic inflammatory diseases such as osteoarthritis, rheumatoid arthritis, ankylosing spondylitis, and gout.

A further presently preferred embodiment of the present invention relates to *Bifidobacterium breve* deposited as DSM 32356 for use in the reduction of intestinal mucosal breaks or lesions.

The invention further relates to a method of supporting the defense against intestinal tissue damage, the method comprising administering the *Bifidobacterium breve* strain deposited as DSM 32356 to a subject in need thereof, such as a subject in need of NSAID treatment. The compositions of the present invention can be used to support the defense against intestinal tissue damage in a subject being in risk of developing intestinal tissue damage e.g. as a result of planned, or ongoing NSAID administration such as low-dose administration of for example acetyl salicylic acid (aspirin).

In a presently preferred embodiment, the *Bifidobacterium breve* deposited as DSM 32356 is for use in a subject who is not treated with PPIs/other antacid drugs, e.g. subjects taking low-dose acetyl salicylic acid (aspirin) as the only medicament.

The *Bifidobacterium breve* deposited as DSM 32356 may be useful during and after NSAID administration, such as acetylsalicylic acid (aspirin), for cardiovascular-protecting properties to lower the risk of heart attack, clot-related strokes and other blood flow problems in patients who have cardiovascular disease or who have already had a heart attack or stroke.

The *Bifidobacterium breve* deposited as DSM 32356 may be useful during and after NSAID administration, such as acetylsalicylic acid (aspirin), for the prevention of cancer and neurodegenerative diseases and for the treatment of other inflammatory conditions. The compositions may also be used to support the defense against intestinal tissue damage in a subject having an increased risk of intestinal tissue damage for other reasons such as intake of coffee, stress, radiotherapy, or medication effects such as selective serotonin re-uptake inhibitors, anticoagulants, alendronate, steroids and immune system suppressants such as chemotherapy. Evidently, the *Bifidobacterium breve* deposited as DSM 32356 can also be used for recovery or reversal of intestinal tissue damage after such exposure.

In a presently preferred embodiment of the present invention the composition of the present invention is used for the reduction of intestinal tissue damage, i.e. by prevention, reduction, or treatment of intestinal mucosal breaks or lesions.

It is contemplated that the *Bifidobacterium breve* deposited as DSM 32356 may also be useful for administration to an infant.

In one embodiment, the compositions comprising *Bifidobacterium breve* deposited as DSM 32356 as described herein may comprise at least one other bacterial strain and/or at least one compound such as vitamins, prebiotics, fibers or other compounds which may have a beneficial health effect such as fructo-oligosaccharides (FOS), galacto-oligosaccharide (GOS) or human milk oligosaccharides.

In a presently preferred embodiment, the compositions comprising *Bifidobacterium breve* deposited as DSM 32356 do not include lysozyme or N-acetylcysteine (NAC).

For example, the compositions of the present invention may comprise bacteria of the *Bifidobacterium breve* strain deposited as DSM 32356 and at least one other bacterial strain.

The compositions of the present invention may comprise bacteria of the strain *Bifidobacterium breve* deposited as DSM 32356 and bacteria of at least one other bacterial strain, wherein the at least one other bacterial strain is selected from the group consisting of *Lactococcus lactis* subsp. *lactis* biovar. *diacetylactis*, *Lactococcus lactis* subsp. *cremoris*, *Lactococcus lactis* subsp. *lactis*, any strain belonging to the genus *Lactobacillus* including but not limited to *Lactobacillus acidophilus*, *Lactobacillus casei* subsp. *casei*, *Lactobacillus delbrueckii* subsp. *bulgaricus*, *Lactobacillus fermentum*, *Lactobacillus gasseri*, *Lactobacillus helveticus*, *Lactobacillus lactis*, *Lactobacillus rhamnosus*, *Lactobacillus salivarius*, any strain belonging to the genus *Bifidobacterium* including but not limited to *Bifidobacterium adolescentis*, *Bifidobacterium angulatum*, *Bifidobacterium animalis* subsp. *lactis*, *Bifidobacterium bifidum*, *Bifidobacterium breve*, *Bifidobacterium catenulatum*, *Bifidobacterium dentium*, *Bifidobacterium infantis*, *Bifidobacterium longum*, *Bifidobacterium magnum*, *Bifidobacterium pseudocatenulatum*, or from the genera of *Akkermansia*, *Anaerostipes*, *Butyricicoccus*, *Christensenella*, *Clostridia*, *Coprococcus*, *Dorea*, *Eubacterium*, *Faecalibacterium* or *Roseburia* or the family Coriobacteriaceae.

In a preferred embodiment the composition does not comprise *Lactobacillus plantarum*.

Thus, the composition may further comprise at least one strain of a bacterium selected from the group comprising *Bifidobacterium animalis* subsp. *lactis* deposited as DSM 15954, *Lactobacillus acidophilus* deposited as DSM 13241, *Lactobacillus rhamnosus* deposited as ATCC 53103, *Lactobacillus rhamnosus* deposited as ATCC 55826, *Lactobacillus reuteri* deposited as ATCC 55845, *Lactobacillus paracasei* subsp. *paracasei* deposited as ATCC 55544, *Lactobacillus paracasei* deposited as LMG-17806, *Streptococcus thermophilus* deposited as DSM 15957, *Lactobacillus fermentum* deposited as NM02/31074, *Lactobacillus paracasei* subsp. *paracasei* deposited as CCTCC M204012.

In presently preferred embodiments, only one, two, three, four or five different strains are present in a composition according to the invention.

In one aspect of this embodiment the compositions of the present invention comprise bacteria of the strain *Bifidobacterium breve*, for example bacteria of the *Bifidobacterium breve* strain deposited as DSM 32356, and bacteria of the strain *Bifidobacterium animalis* subsp. *lactis*, for example bacteria of the *Bifidobacterium animalis* subsp. *lactis* strain deposited as DSM 15954. The composition may comprise bacteria of these two strains as the only probiotic component.

In another aspect of this embodiment the compositions of the present invention comprise bacteria of the strain *Bifidobacterium breve*, for example bacteria of the *Bifidobacterium breve* strain deposited as DSM 32356, and bacteria of the strain *Lactobacillus rhamnosus*, for example bacteria of the *Lactobacillus rhamnosus* strain deposited as ATCC 53103. The composition may comprise bacteria of these two strains as the only probiotic component.

In a further embodiment the compositions of the present invention comprise bacteria of the strain *Bifidobacterium breve*, for example bacteria of the *Bifidobacterium breve* strain deposited as DSM 32356, bacteria of the strain *Bifidobacterium animalis* subsp. *lactis*, for example bacteria of the *Bifidobacterium animalis* subsp. *lactis* strain deposited as DSM 15954 and bacteria of the strain *Lactobacillus rhamnosus*, for example bacteria of the *Lactobacillus rhamnosus* strain deposited as ATCC 53103. The composition may comprise bacteria of these three strains as the only probiotic component.

In a yet another aspect of this embodiment, the compositions of the present invention comprise bacteria of the strain *Bifidobacterium breve*, for example bacteria of the strain *Bifidobacterium breve* deposited as DSM 32356, bacteria of the strain *Bifidobacterium infantis*, and bacteria of the strain *Bifidobacterium longum*. The composition may comprise bacteria of these three strains as the only probiotic component.

In a yet further aspect of this embodiment, the compositions of the present invention comprise bacteria of the strain *Bifidobacterium breve* deposited as DSM 32356, bacteria of the strain *Bifidobacterium infantis*, bacteria of the strain *Bifidobacterium longum*, and bacteria of the strain *Bifidobacterium bifidum*. The composition may comprise bacteria of these four strains as the only probiotic component.

In a yet further aspect of this embodiment, the compositions of the present invention comprise bacteria of the strain *Bifidobacterium breve* deposited as DSM 32356, bacteria of the strain *Bifidobacterium infantis*, bacteria of the strain *Bifidobacterium longum*, bacteria of the strain *Bifidobacterium bifidum*, and bacteria of the strain *Bifidobacterium catenulatum*. The composition may comprise bacteria of these five strains as the only probiotic component.

In one embodiment of this aspect bacteria of the *Bifidobacterium breve* strain deposited as DSM 32356 are the only probiotic component in the composition.

The compositions of the present invention may comprise the bacteria in any suitable form for administration to the subject. In a preferred embodiment, the compositions of the present invention may comprise the bacteria in dried form, which can be obtained by freeze-drying, spray-drying or lyophilization.

If the bacteria are freeze-dried, they are generally mixed with a cryoprotectant before they are freeze-dried in order to obtain a high viability. The term "a cryoprotectant" is used in the context of the present invention to refer to a substance that is able to improve the survival during freezing and/or drying and to improve the storage stability of bacteria. The cryoprotectant used herein preferably comprises a saccharide or a sugar alcohol such as inositol.

The saccharide may be a mono-, di-, oligo- or polysaccharide, or a mixture of at least two saccharides. Useful monosaccharides include glucose (also known as dextrose), fructose, ribose and galactose and useful disaccharides include among other sucrose, trehalose, maltose and lactose. The composition may comprise one or more mono- or disaccharides, such as one, two, or three or even more different saccharides.

As an example, the cryoprotectant may comprise a mixture of a disaccharide, such as sucrose, and a polysaccharide, such as maltodextrin.

The cryoprotectant may further comprise a peptide, protein, protein hydrolysate or a mixture thereof. Examples of peptides and proteins to be used are casein, pea, whey, albumin, glutamic acid or gelatin, and any isolate or hydrolysate thereof. Other additives, e.g. antioxidants such as sodium ascorbate, sodium citrate, trisodium citrate dihydrate and cysteine hydrochloride may also be present. Skim milk powder and yeast extract may also be ingredients.

In one embodiment, the composition of the present invention comprises bacteria of the *Bifidobacterium breve* strain deposited as DSM 32356 in frozen or freeze-dried form and a cryoprotectant. The cryoprotectant may comprise a saccharide. In a particularly preferred aspect of this embodiment, the cryoprotectant may comprise a mixture of a disaccharide, such as sucrose, and a polysaccharide, such as maltodextrin.

The composition of the present invention may comprise at least one compound such as an NSAID. Examples of NSAIDs which may be combined with the *Bifidobacterium breve* strain deposited as DSM 32356 according to the present invention may be one or more of the following NSAIDs: acetylsalicylic acid (aspirin), ibuprofen, ketoprofen, naproxen sodium, diclofenac potassium, diclofenac sodium, etodolac, flurbiprofen, indomethacin, ketorolac, nabumetone, naproxen, oxaprozin, piroxicam, sulindac, celecoxib, mefenamic acid, and etoricoxib. The compositions may be formulated as combined or as separate compositions of the bacterial strain or strains and the compound e.g. the NSAID such as acetylsalicylic acid (aspirin).

It is preferred that the compositions of the present invention are administered orally. The compositions are thus typically in a form suitable for oral administration. The composition may be a solid or a liquid composition. The composition may be in unit dosage form. For example, the composition can be a capsule, pastille, a pill, a tablet, a soft gel, a sachet, a stick, a stick powder, or in a more general composition such as oil drops, an emulsion or a paste, or in any other suitable carrier determined by those of skill in the art to be an effective carrier for live organisms.

The compositions may be encapsulated for example using a suitable polymeric matrix to improve long-term stability and storage of the compositions. Those skilled in the art will appreciate that any suitable encapsulation material or matrix and encapsulation methods and techniques known to those skilled in the art may be used.

The composition may be included in a dietary supplement or pharmaceutical composition or may be part of a feed product or a food product such as a fermented milk product e.g. a yogurt or an infant formula.

In a further embodiment, the compositions of the present invention comprise bacteria of the *Bifidobacterium breve* strain deposited as DSM 32356 in a unit dosage form or a more general composition as described above or as part of a dietary supplement or a feed or food product such as a fermented milk product e.g. a yogurt or an infant formula.

In one embodiment of the present invention, the composition of the present invention may be used as a prophylactic treatment to support the defense against intestinal tissue damage in a subject having an increased risk of intestinal tissue damage. In another embodiment of the present invention, the composition of the present invention may be used as a treatment to support the defense against intestinal tissue damage in a subject having intestinal tissue damage.

As used herein the terms "treating" and "treatment" refer to all applications which alleviate, remedy, or otherwise hinder, retard, heal, or reverse the progression of, a disease or disorder or at least one symptom of a disease or disorder, including reducing the severity of a disease or disorder. Thus, treatment does not necessarily imply that a subject is treated until complete recovery from a disease or disorder. Similarly, the terms "prophylactic", "preventing", "prevention" and the like refer to any and all applications that prevent intestinal tissue damage in a subject, which may lead to the establishment of a disease or disorder.

The term "subject" as used herein refers to any mammal, including, but not limited to, livestock and other farm animals (such as cattle, goats, sheep, horses, pigs and chickens), performance animals (such as racehorses), companion animals (such as cats and dogs), laboratory test animals and humans. Typically, the subject is a human.

In one embodiment of the present invention, the *Bifidobacterium breve* of the present invention may be administered in an amount of at least $1 \times 10^6$ CFU/day. Preferred amounts are at least $1 \times 10^6$ CFU/day, at least $1 \times 10^7$ CFU/day, at least $1 \times 10^8$ CFU/day, at least $1 \times 10^9$ CFU/day, at least $1 \times 10^{10}$ CFU/day, at least $1 \times 10^{11}$ CFU/day, at least $1 \times 10^{12}$ CFU/day.

In one embodiment of the present invention, the *Bifidobacterium breve* of the present invention and the at least one other strain, if applicable, may be administered in an amount of at least $1 \times 10^6$ CFU/day. Preferred amounts are at least $1 \times 10^6$ CFU/day, at least $1 \times 10^7$ CFU/day, at least $1 \times 10^8$ CFU/day, at least $1 \times 10^9$ CFU/day, at least $1 \times 10^{10}$ CFU/day, at least $1 \times 10^{11}$ CFU/day, at least $1 \times 10^{12}$ CFU/day.

In one embodiment, the composition of the present invention comprises bacteria of the *Bifidobacterium breve* strain deposited as DSM 32356 in dried, frozen or freeze-dried form and the composition is administered in an amount of from $1 \times 10^8$ CFU/day to $1 \times 10^{11}$ CFU/day.

In a presently preferred embodiment, the composition of the present invention comprises bacteria of the *Bifidobacterium breve* strain deposited as DSM 32356 in dried, frozen or freeze-dried form as the only probiotic product and the composition is administered in an amount of from $1 \times 10^8$ CFU/day to $1 \times 10^{11}$ CFU/day.

Those skilled in the art will appreciate that the administration of compositions disclosed herein can be carried out with dose levels and dosing regimens as required depending on the circumstances and on the condition of the subject. Suitable dosage regimes can be determined based on the teaching of the present application. Dosage regimens may be adjusted to provide the optimal support against intestinal tissue damage of the subject. Persons skilled in the art will appreciate that the exact amounts and rates of administration of the *Bifidobacterium breve* strain will depend on a number of factors such as the age, body weight, general health, sex and dietary requirements of the subject. Based on the teaching herein those skilled in the art will, by routine trial and experimentation, can determine suitable dosage regimes on a case-by-case basis.

In an exemplary embodiment of the present invention, the composition of the present invention may be administered daily for at least 1 day. Alternatively, the composition can be administered once or more daily for at least 1 day, 2 days, 4 days, 1 week, 2 weeks, 3 weeks, 4 weeks, 5 weeks, 6 weeks, 7 weeks, 8 weeks, 9 weeks, 10 weeks or more.

Accordingly, the present invention provides a composition of the present invention comprising bacteria of the *Bifidobacterium breve* strain deposited as DSM 32356 in dried, frozen or freeze-dried form wherein the composition is administered in a dosage of from $1 \times 10^8$ CFU/day to $1 \times 10^{11}$ CFU/day for at least 2 weeks.

In a separate embodiment, the present invention provides a composition of the present invention comprising bacteria of the *Bifidobacterium breve* strain deposited as DSM 32356 in dried, frozen or freeze dried from wherein the composition is orally administered in an amount of from $1 \times 10^8$ CFU/day to $1 \times 10^{11}$ CFU/day for at least 8 weeks.

In a further aspect the present invention provides a combination treatment comprising a composition which comprises *Bifidobacterium breve* bacteria of the *Bifidobac-*

*terium breve* strain deposited as DSM 32356, and at least one compound as described herein for co-administration to a subject in need thereof. The compositions may be formulated as combined or as separate compositions of the bacterial strain or strains and the compound e.g. the NSAID.

In a separate embodiment, the *Bifidobacterium breve* strain is incorporated into a feed or food product such as an infant formula, health food, food additive, dietary supplement, pharmaceutical or over-the-counter formulation in a solid form such as a powder, a tablet, or a liquid form.

In a preferred embodiment, the strain of *Bifidobacterium breve* is present in a concentration of at least $10^6$ CFU/g. Specifically, the concentration may be at least $1\times10^6$ CFU/g, at least $1\times10^7$ CFU/g, at least $1\times10^8$ CFU/g, at least $1\times10^9$ CFU/g, at least $1\times10^{10}$ CFU/g, at least $1\times10^{11}$ CFU/g or at least $1\times10^{12}$ CFU/g.

In one embodiment, the strain of *Bifidobacterium breve* and the at least one other strain are present in a concentration of at least $10^6$ CFU/g. Specifically, the concentration may be at least $1\times10^6$ CFU/g, at least $1\times10^7$ CFU/g, at least $1\times10^8$ CFU/g, at least $1\times10^9$ CFU/g, at least $1\times10^{10}$ CFU/g, at least $1\times10^{11}$ CFU/g or at least $1\times10^{12}$ CFU/g.

In a further aspect, the present invention provides a method for producing a feed or food product, dietary supplement or pharmaceutical composition comprising producing bacteria of the *Bifidobacterium breve* strain deposited under number DSM 32356, and incorporating the same into a food product, dietary supplement or pharmaceutical composition in a concentration of at least $10^6$ CFU/g.

Deposit and Expert Solution

The applicant requests that a sample of the micro-organism deposited for the present application as described below may only be made available to an expert, until the date on which the patent is granted.

*Bifidobacterium breve* was deposited with DSMZ-Deutsche Sammlung von Mikroorganismen and Zellkulturen GmbH, Inhoffenstr. 7B, D-38124 Braunschweig, on Aug. 9, 2016 under the accession no. DSM 32356.

LEGEND TO FIGURES

FIG. 1

FIG. 1 shows an overview of the gastrointestinal tract, i.e. the stomach, the small intestine comprising the duodenum, jejunum and ileum, and the large intestine (colon).

FIG. 2

FIG. 2 illustrates the transepithelial electrical resistance (TEER) as percentage of baseline over time, dots are means, error bars are SDs (A) and TEER area-under-the-curve (AUC) from 0-15 hrs, bars are means and error bars are SDs (B). ****p<0.0001.

FIG. 3

In vitro cytokine expression of *Bifidobacterium breve* DSM 32356-stimulated dendritic cells from 4 donors. Data are expressed as mean±SEM in pg/ml. A. Secretion of IL-10, B. Secretion of IL-12p70 C. IL-10:IL-12p70 ratio. ****p<0.0001.

FIG. 4

Figure 4:
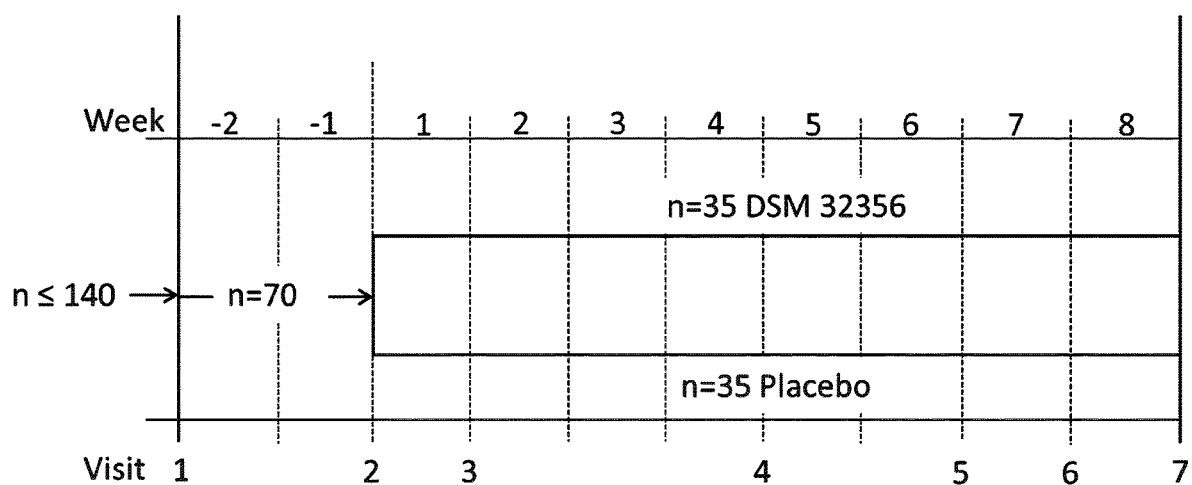

FIG. 4 shows the clinical trial design and visit overview. Visit 1 was a screening visit. Subjects then entered a 2-week run-in period before baseline measurements were made at visit 2 at which subjects were randomized to active DSM 32356 or placebo treatment. Intake of trial product began the morning after visit 2. Subjects were also instructed to take 300 mg of acetylsalicylic acid (aspirin) daily from the same morning for the first 6 weeks of the DSM 32356/placebo intervention. Pillcam capsule endoscopy was performed at Visits 2-7.

FIG. 5

Figure 5A:
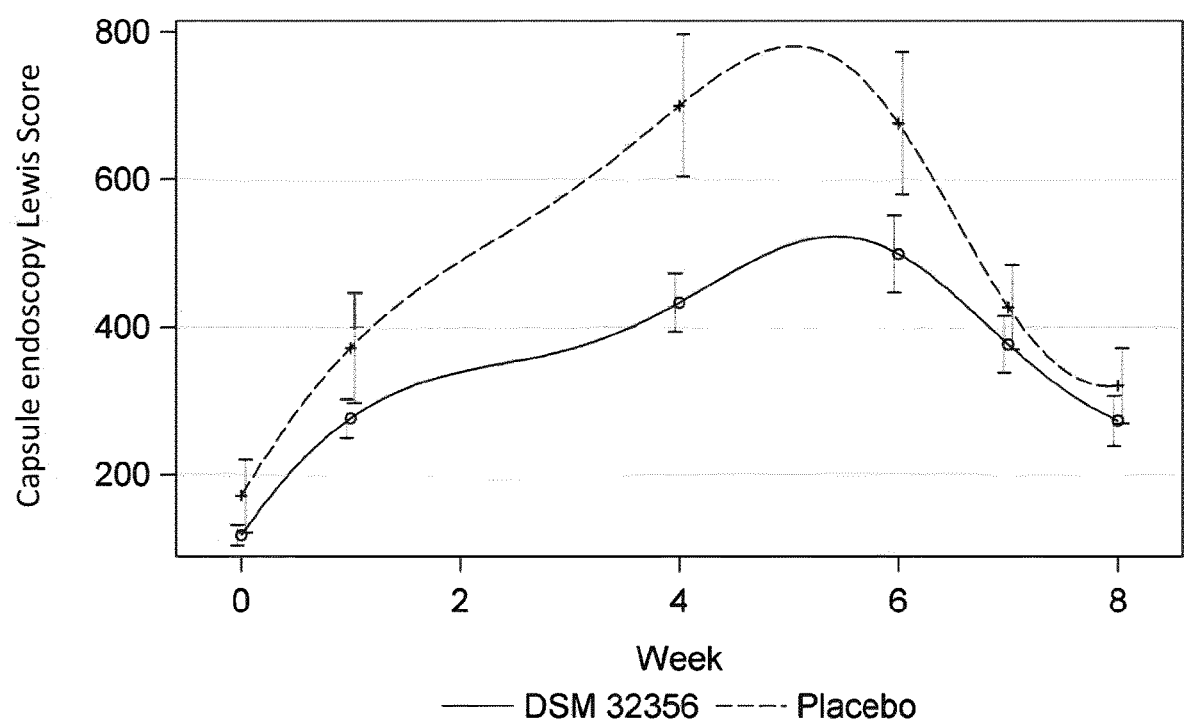
Figure 5B:
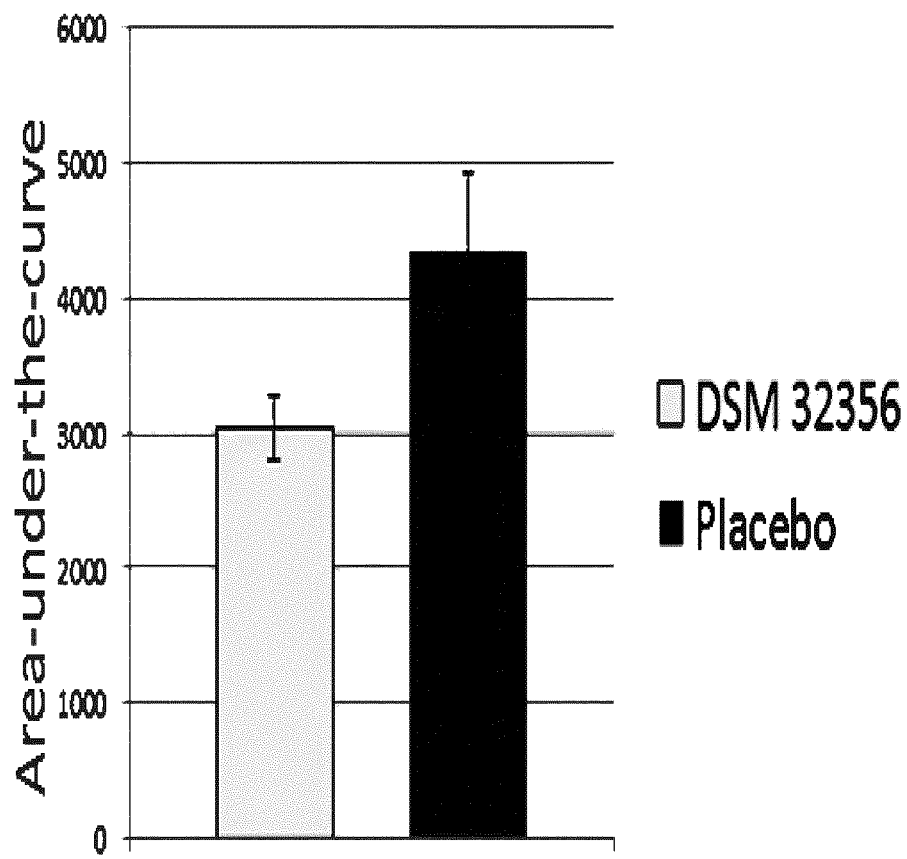

FIG. 5 shows the assessment of the primary endpoint, area-under-the-curve for the Capsule Endoscopy Lewis Score. FIG. 5a shows curve dynamics for the two arms and FIG. 5b the area-under-the-curve illustrated as mean value bar charts with a p value of <0.05 (*) (error bars being ±SEM).

FIG. 6

Figure 6A:
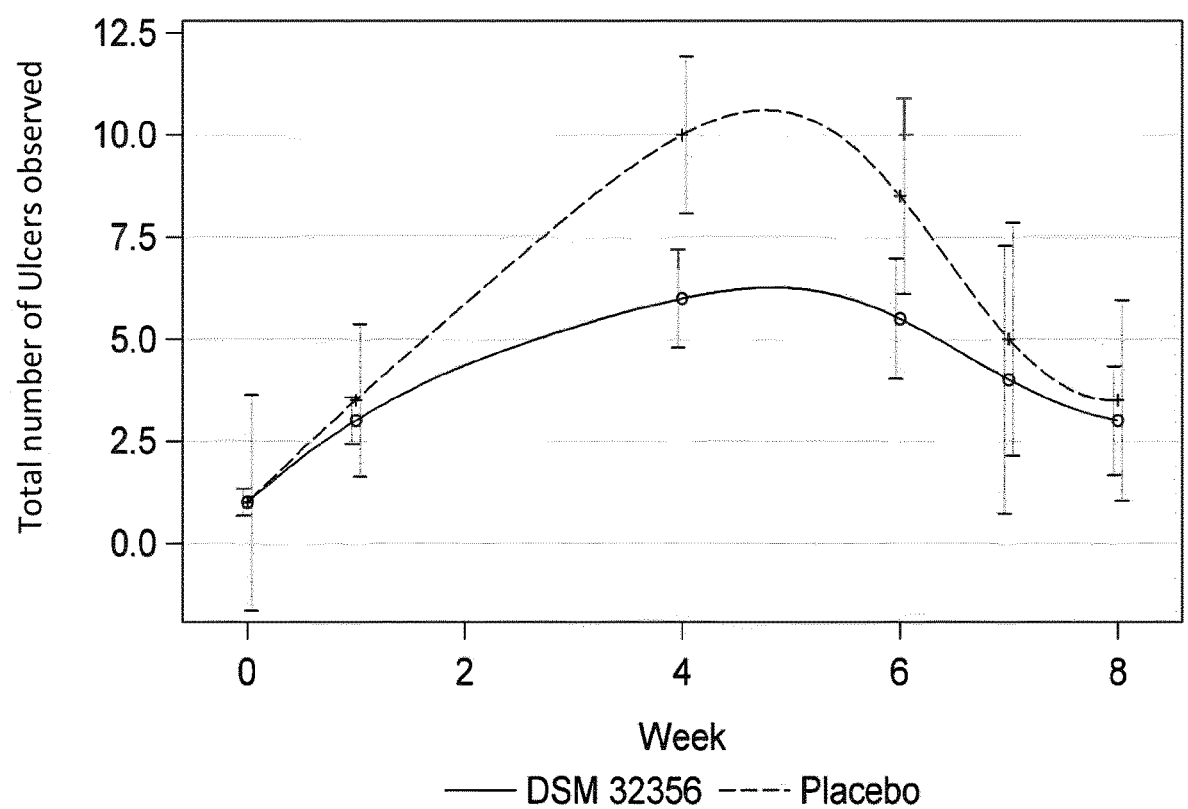
Figure 7A:
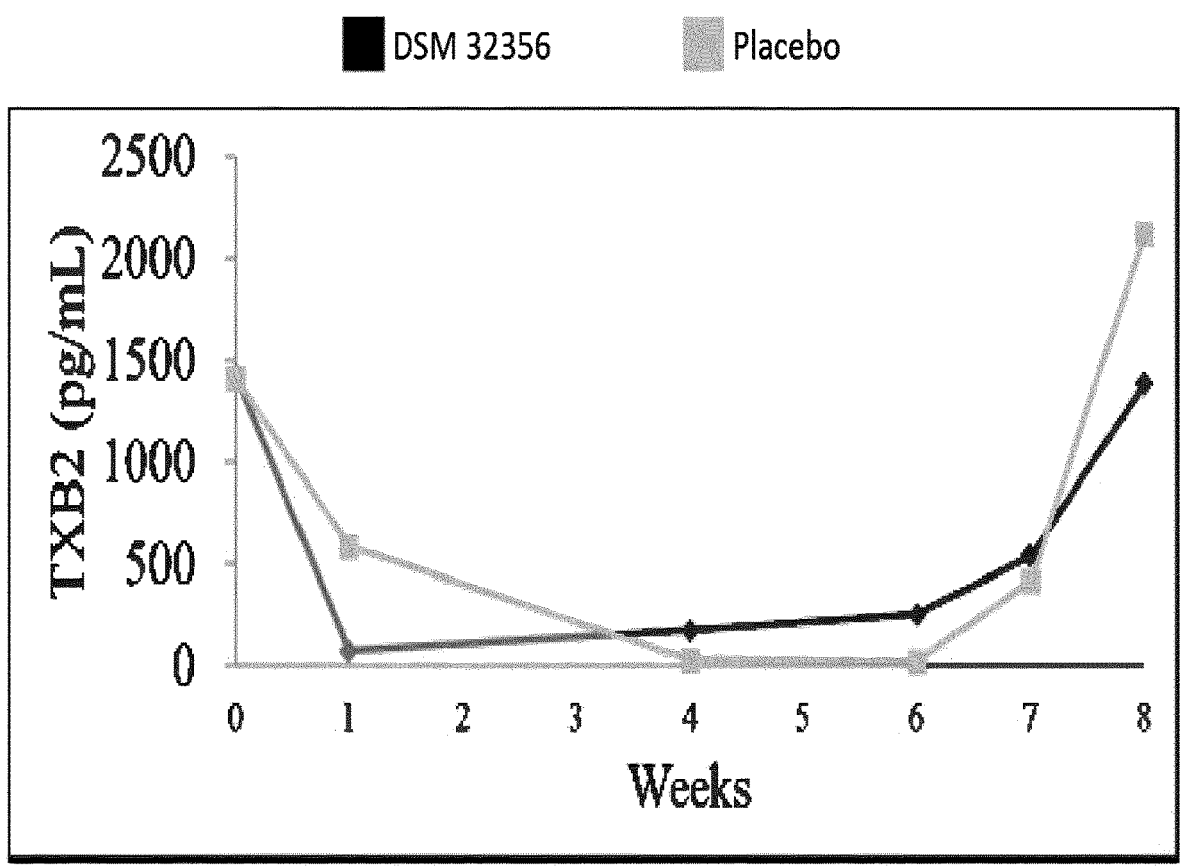
Figure 7B:
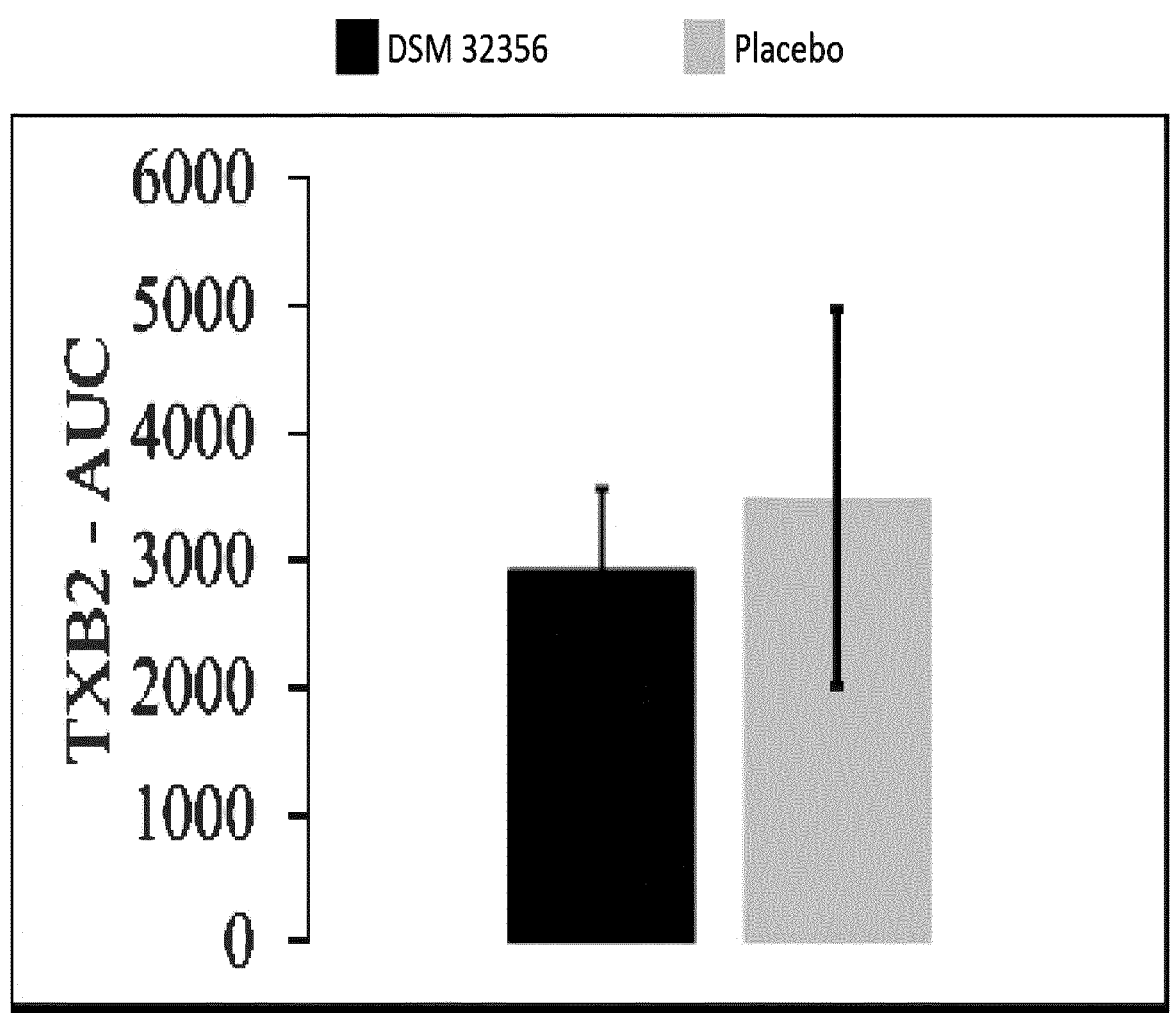
Figure 7C:
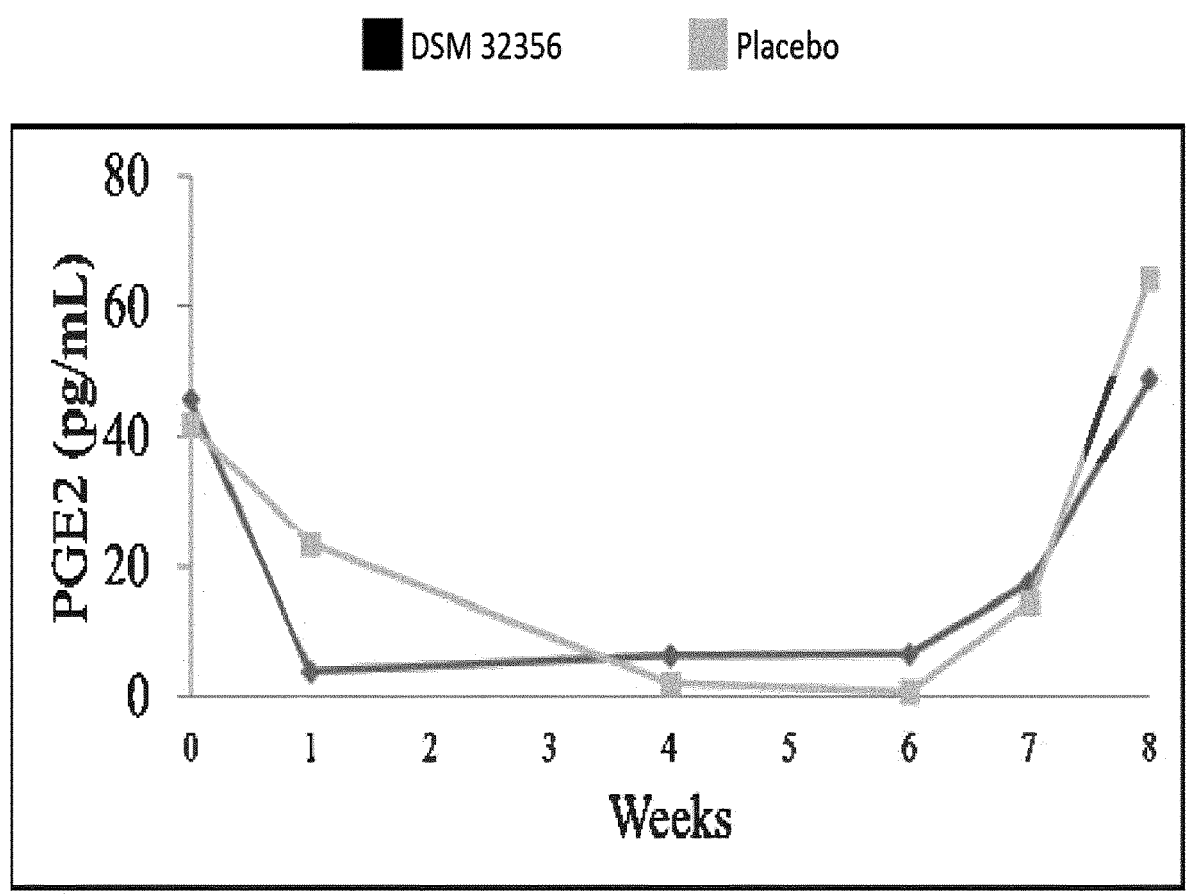
Figure 7D:
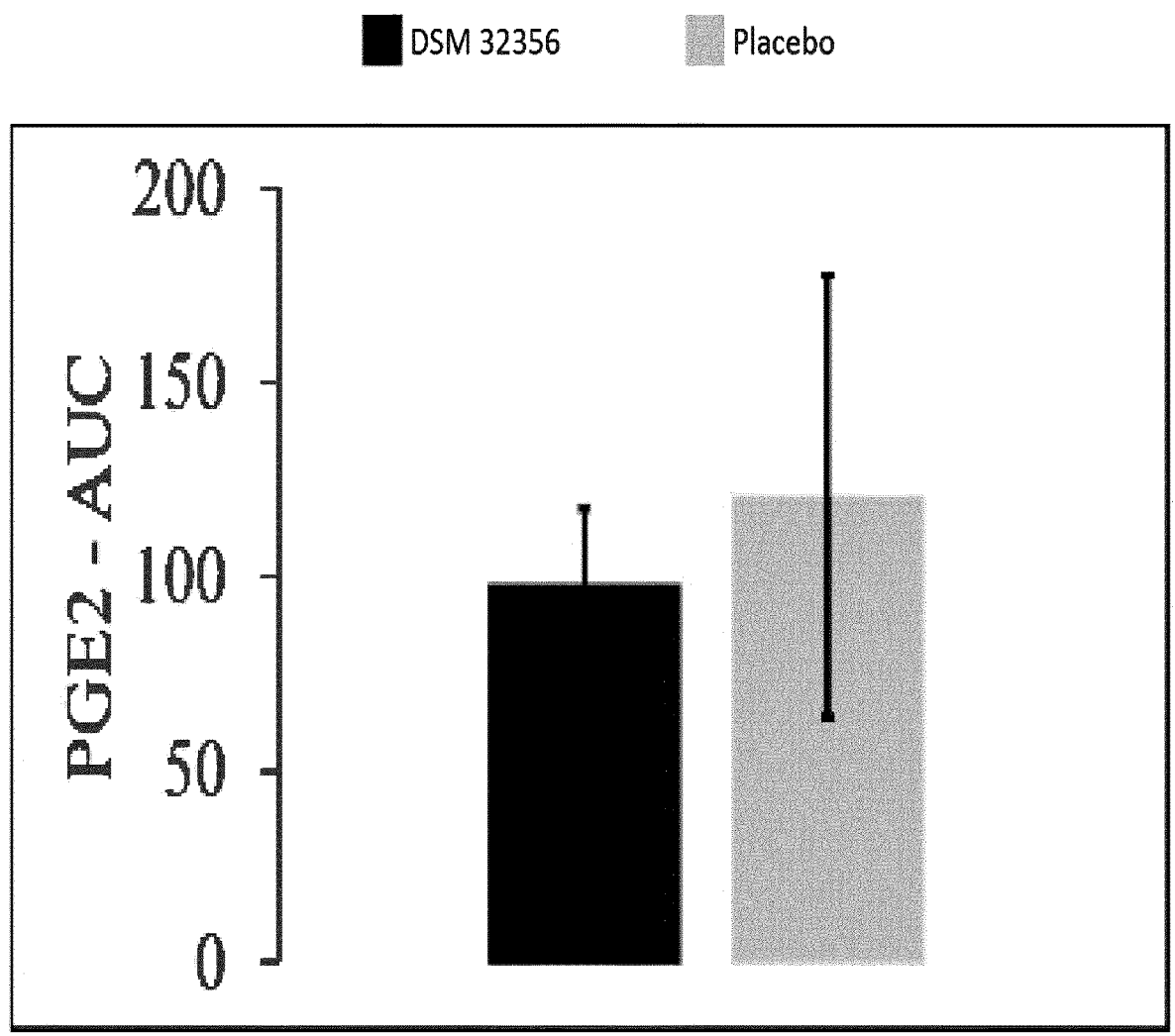
Figure 9:
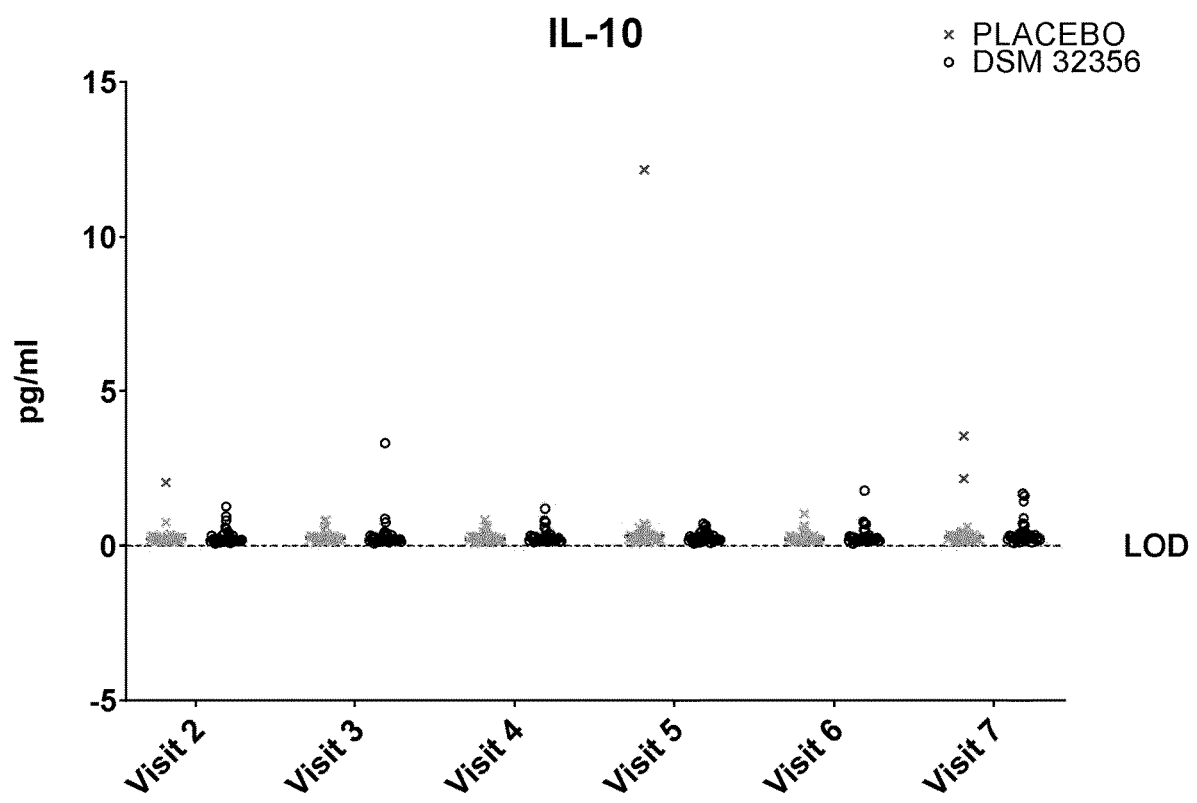
Figure 10:
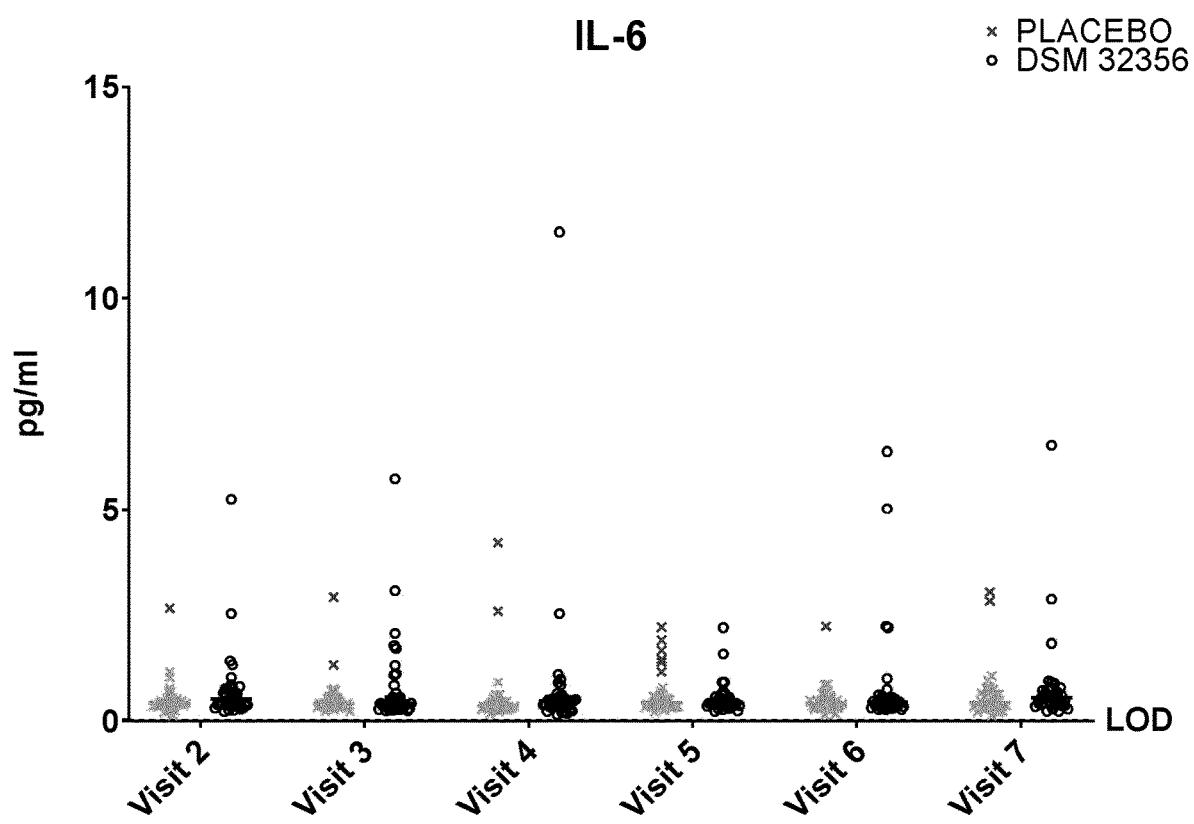
Figure 11:
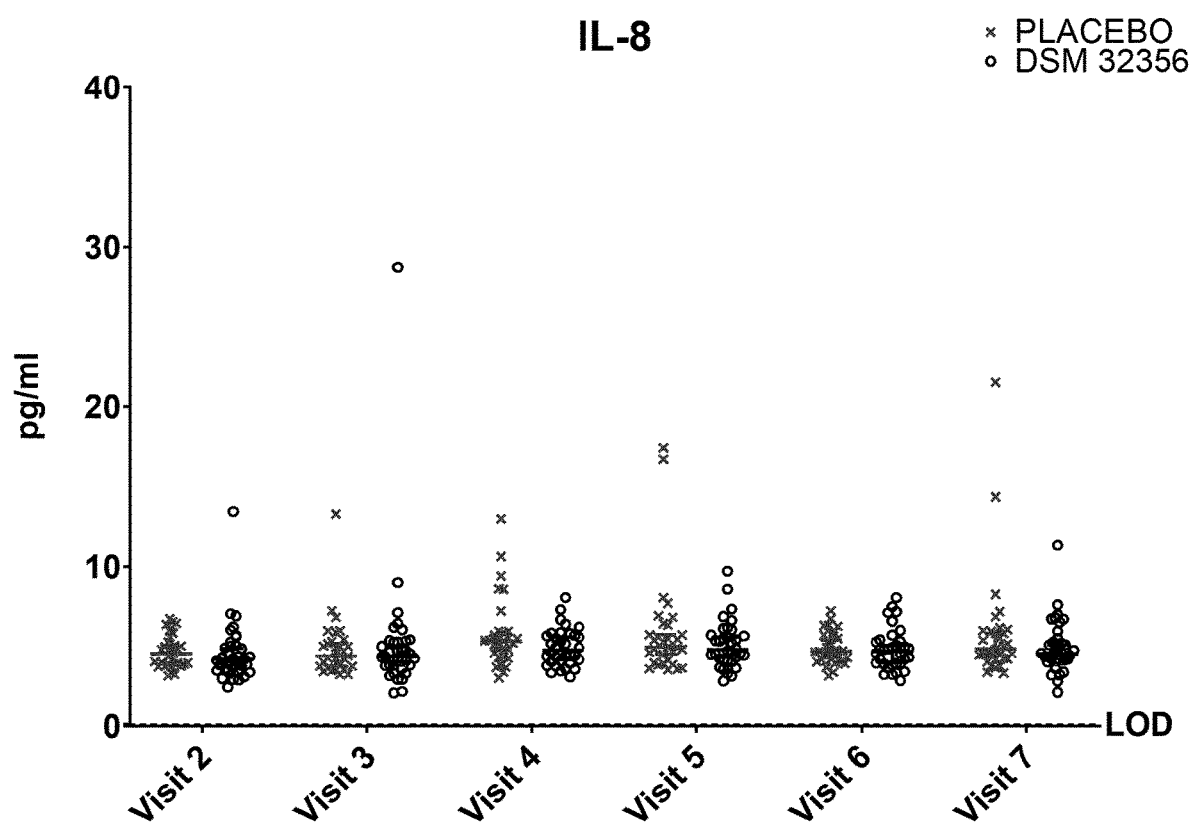
Figure 12:
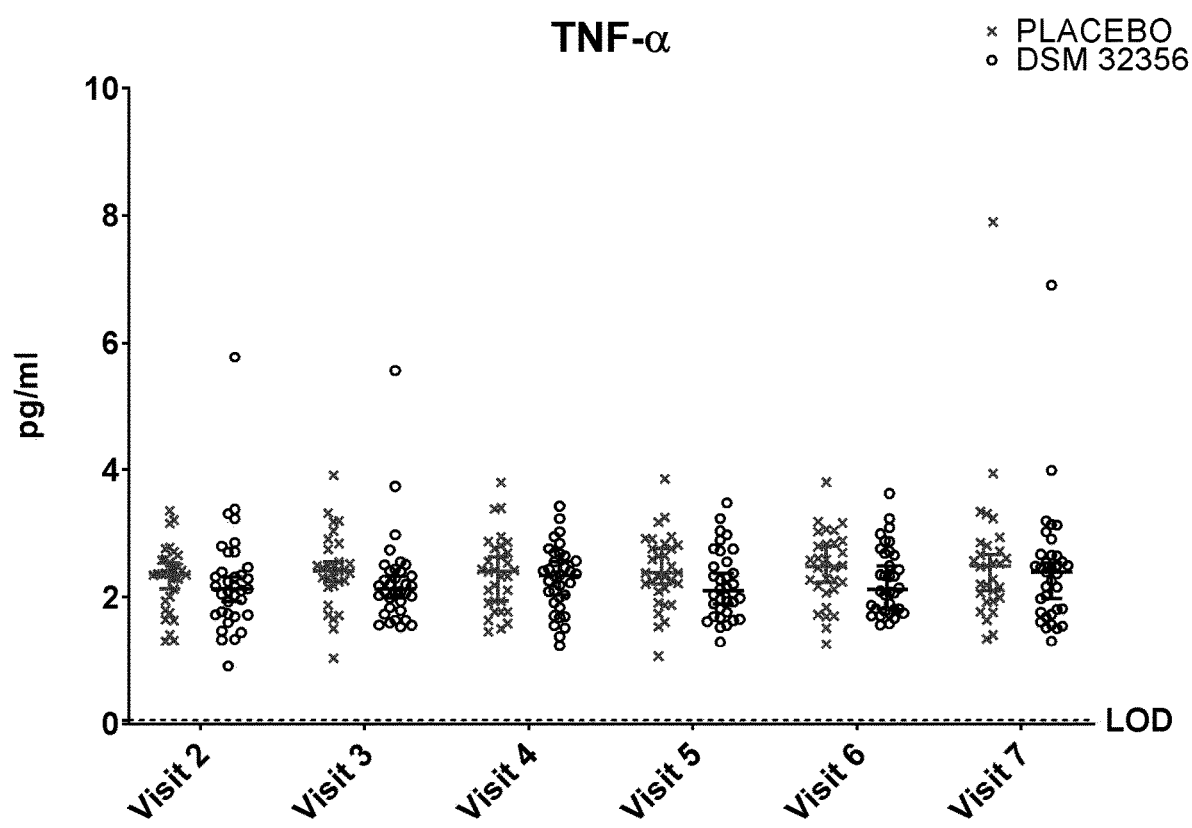
Figure 13:
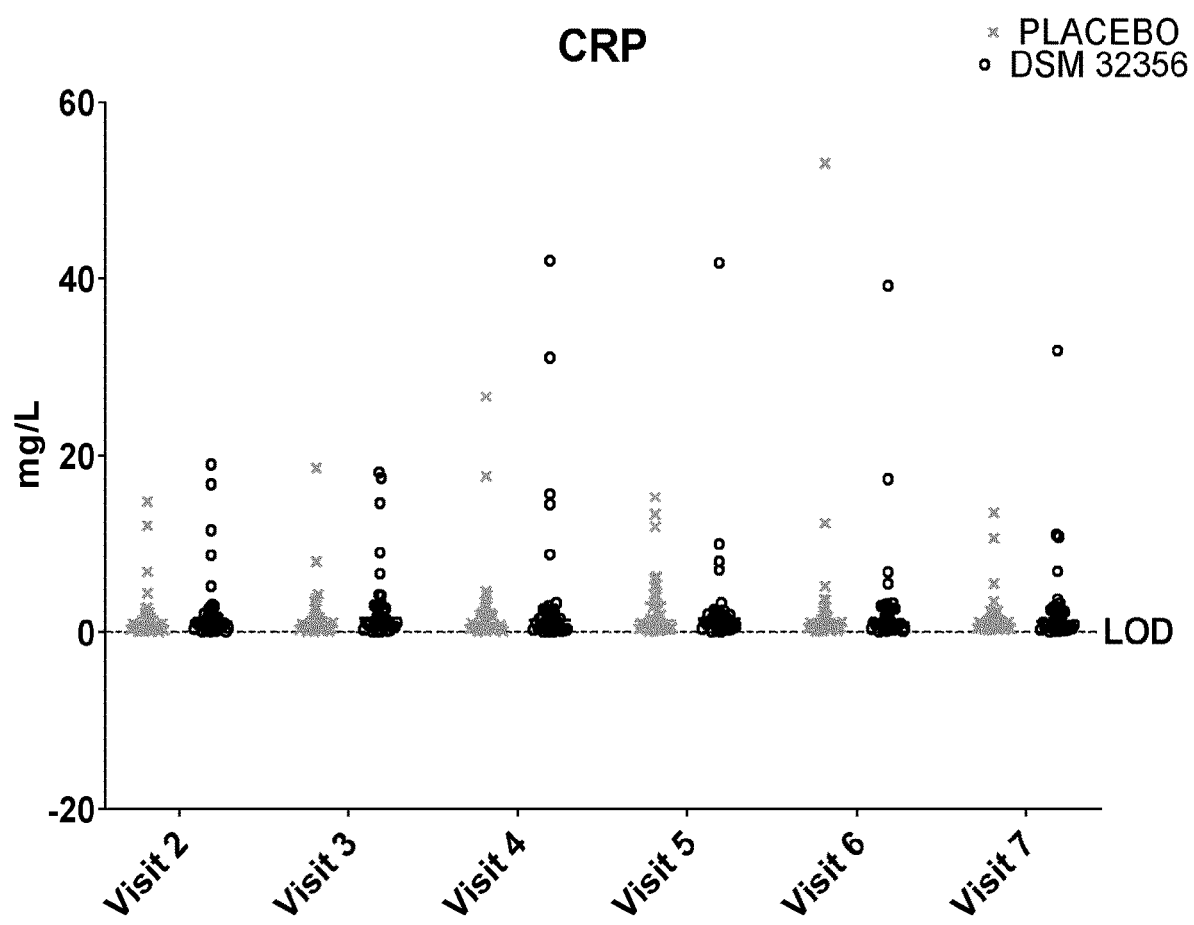

FIG. 6 shows the assessment of the first secondary endpoint, area-under-the-curve for the total number of ulcers as assessed by capsule endoscopy. FIG. 6a shows curve dynamics for the two arms and FIG. 6b the area-under-the-curve illustrated as mean bar charts with a p value of <0.05 (error bars being ±SEM).

FIG. 7

FIG. 7 shows mean serum concentrations of Thromboxane B2 (TXB2) per visit (A), AUC ±SEM (B), mean serum concentrations of Prostaglandin E2 (PGE2) per visit (C) and AUC ±SEM (D).

FIG. 8

IFN-γ levels in plasma of subjects belonging to the placebo or *Bifidobacterium breve* DSM 32356 group. Data are expressed as median +95% CI in pg/ml.

FIG. 9

IL-10 levels in plasma of subjects belonging to placebo or *Bifidobacterium breve* DSM 32356 group. Data are expressed as median +95% CI in pg/ml.

FIG. 10

IL-6 levels in plasma of subjects belonging to placebo or *Bifidobacterium breve* DSM 32356 group. Data are expressed as median +95% CI in pg/ml.

FIG. 11

IL-8 levels in plasma of subjects belonging to placebo or *Bifidobacterium breve* DSM 32356 group. Data are expressed as median +95% CI in pg/rd.

FIG. 12

TNF-α levels in plasma of subjects belonging to placebo or *Bifidobacterium breve DSM*32356 group. Data are expressed as median +95% CI in pg/ml.

FIG. 13

C-Reactive Protein (CRP) levels in plasma of subjects belonging to placebo or *Bifidobacterium breve* DSM 32356 group. Data are expressed as median +95% CI in mg/L.

FIG. 14

Figure 14:
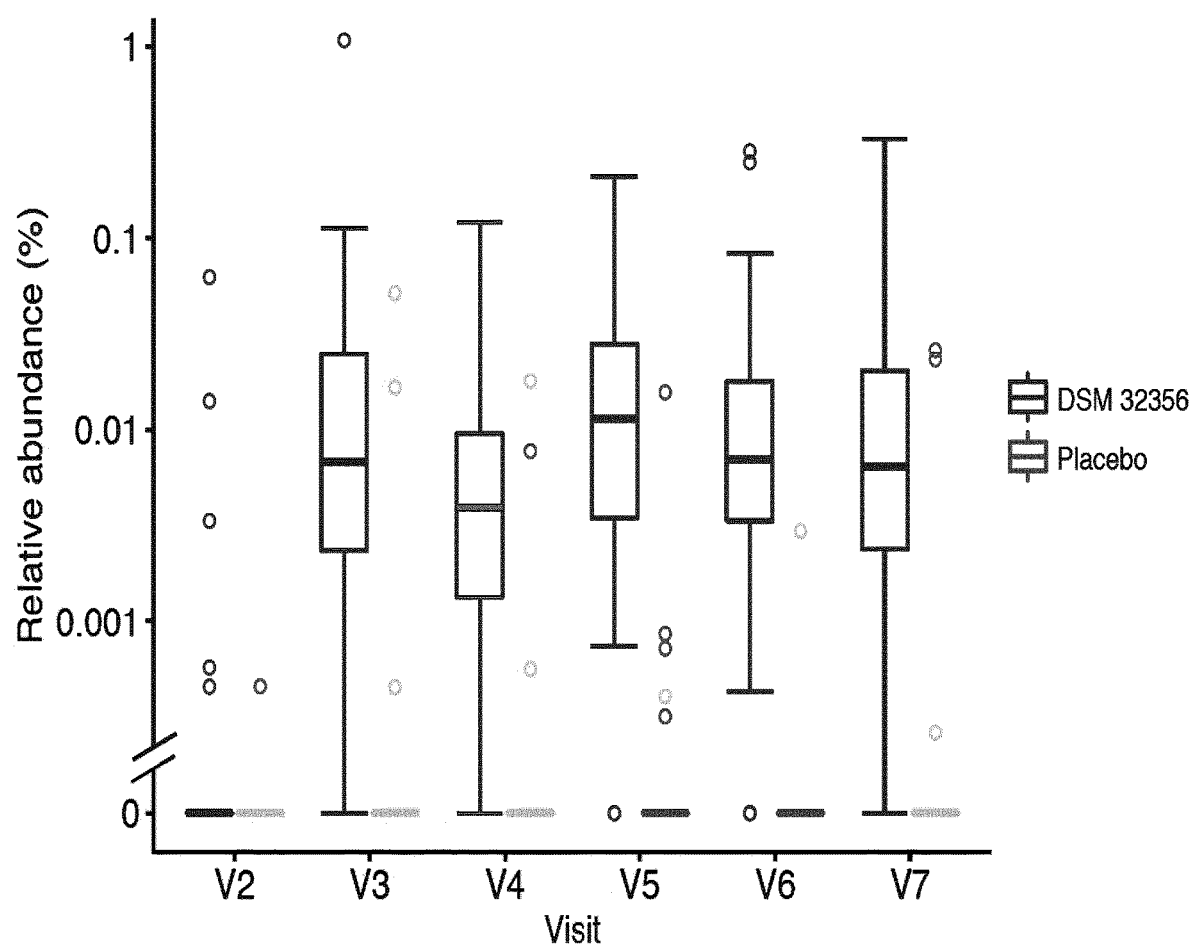

FIG. 14 shows Box-plot representing the relative abundance in percent of *Bifidobacterium breve* in stool in the *Bifidobacterium breve* DSM 32356 treated and placebo groups. The boxed extends from the first quartile (Q1) to the third quartile (Q3) and the line within the box shows the median value. The lower whisker extends to the smallest value within Q1−1.5× inter-quartile range (IQR) and the upper whisker extends to the largest value within Q3+1.5× IQR. Values outside the whiskers are shown as circles.

FIG. 15

Figure 15:
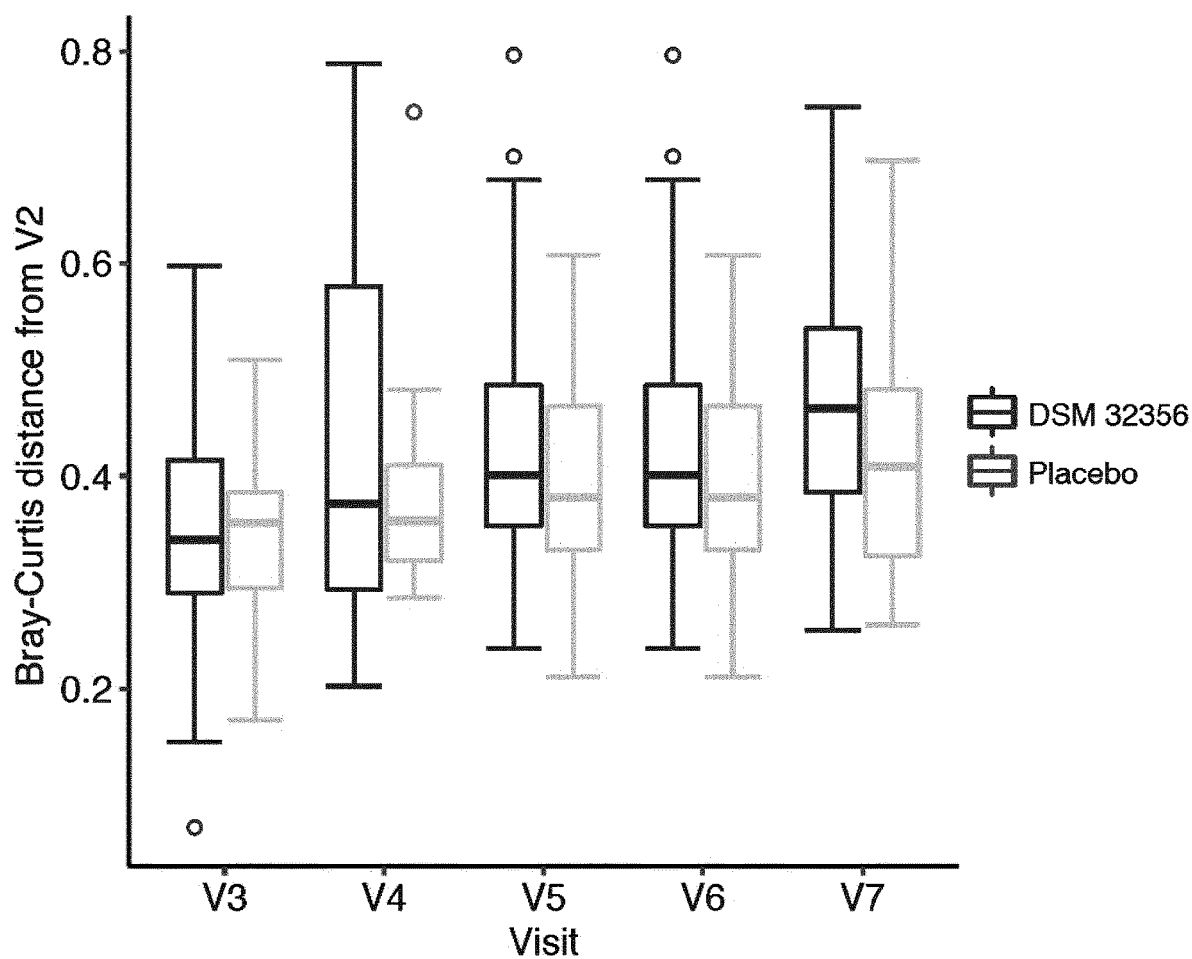

FIG. 15 shows a Box-plot with the Bray-Curtis dissimilarity of stool microbial composition for the *Bifidobacterium breve* DSM 32356 and placebo groups, comparing Visit 2 with later visits (V3-V7). The boxed extends from the first quartile (Q1) to the third quartile (Q3) and the line within the box shows the median value. The lower whisker extends to the smallest value within Q1−1.5× inter-quartile range (IQR) and the upper whisker extends to the largest value within Q3+1.5×IQR. Values outside the whiskers are shown as circles.

FIG. 16

Aspirin and salicylic acid concentrations for the 2 different dilutions rows, A) dilution row A inoculated with *Bifidobacterium breve* DSM 32356 and B) dilution row B where pH was adjusted to a final pH of 4.5.

EXAMPLES

Example 1

Analysis of Antibiotic Susceptibility and Cytotoxic Activity

Antibiotic susceptibility of DSM 32356 was determined by measuring the minimum inhibitory concentrations (MICs) of a number of antibiotics according to the ISO 10932 IDF 223 international standard.

The test performed was a broth microdilution method using VetMIC Lact-1 and Lact-2 panels (National Veterinary Institute of Sweden, Uppsala, Sweden) and growth in LSM medium (ISO-sensitest medium (Oxoid) supplemented with 10% MRS (de Man, Rogosa and Sharpe) broth (BD Difco 288110, UK) with 0.05% Cysteine hydrochloride (CyHCl) (Merck 102839, Germany for 48 hours at 37° C. under anaerobic conditions with three biological replicates. The range of antibiotics tested complies with the European Food Safety Authority (EFSA) "Guidance on the characterisation of microorganisms used as feed additives or as production organisms" (EFSA Journal 2018, 16:5206) for the 25 *Bifidobacterium* group.

DSM 32356 was found to be sensitive to all antibiotics relevant for the *Bifidobacterium* group according to the EFSA guideline (gentamycin, streptomycin, tetracycline, erythromycin, clindamycin, chloramphenicol, ampicillin, and vancomycin) with MIC values below the EFSA 2018 cut-off values.

The genome of DSM 32356 was analyzed for antibiotic resistance genes by screening against the curated database ResFinder which contains more than 2,200 resistance genes (Zankari, E., Hasman, H., Cosentino, S., Vestergaard, M., Rasmussen, S., Lund, O., et al. (2012) Identification of acquired antimicrobial resistance genes. *J. Antimicrob. Chemother.* 67: 2640-2644). The database was downloaded and imported into CLC Main Workbench version 8.0.1 on Feb. 8, 2019. The genome was screened for resistance genes against the ResFinder database using megaBLAST settings (Expect threshold 10, word size 28). In agreement with DSM 32356 being phenotypically sensitive to all antibiotics tested, no antibiotic resistance genes were identified in the genome of DSM 32356.

DSM 32356 was tested for cytotoxic activity using a Vero cell assay method based on the EFSA guidance "Guidance on the assessment of the toxigenic potential of *Bacillus* species used in animal nutrition" (EFSA Journal 2014, 12:3665). DSM 32356 was grown at 37° C. under anaerobic conditions in MRS broth (BD Difco 288110, UK) with 0.05% Cysteine hydrochloride (CyHCl) (Merck 102839, Germany. Culture supernatants were isolated after 24 and 48 hours by centrifugation and analyzed for cytotoxicity at Bioneer A/S, Hoersholm, Denmark using the Vero cell assay. DSM 32356 was found to be non-cytotoxic.

Example 2

Intestinal barrier improvements measured in vitro by bacterial ability to increase the electrical resistance across Caco-2 cell monolayer, measured by transepithelial electrical resistance (TEER)

Culturing of Caco-2 Cells

The human intestinal epithelial Caco-2 cell line (DSMZ ACC 169, Leibniz-Institut DSMZ-Deutsche Sammlung von Mikroorganismen und Zellkulturen GmbH, Braunschweig, Germany) was cultured in MEM (Gibco 11095) supplemented with 20% heat inactivated fetal bovine serum (Gibco 10500), 1×MEM non-essential amino acids (Biowest X0557-100) and 1×Pen-Strep-Amp B (Biological Industries 03-033-1B) at 5% $CO_2$ at 37° C. Caco-2 cell passages 7-30 were used. When the cells were approximately 50% confluent the medium was removed, and the cells were washed twice in Hanks' balanced salt solution (HBSS, 1x, Gibco 14175). The cells were trypsinized by adding 2 mL of trypsin (TrypLE Trypsin, Gibco 12604) and left for 4 min in the $CO_2$ incubator at 37° C. Approximately 10 mL of medium was added to the trypsinized cells, they were counted and a concentration of 100.000 cells/mL in supplemented MEM was prepared. A volume of 500 µL of cell suspension was used to seed each apical compartment of transwell-Clear, Polyester Membranes (12 well, 0.4 µM, Costar, Cat. No. 3460), where after 1.5 mL of supplemented MEM was added to the basolateral compartment. Cells were cultured on the inserts for 21 days with change of medium twice a week. After 22 days the transwells were moved to the CellZscope (NanoAnalytics, Germany). The medium was changed to antibiotics (Abx) free medium adding 1.65 and 0.76 mL of Abx-free medium in the basolateral and apical compartments, respectively. The CellZscope was placed overnight in a $CO_2$ incubator (5%) at 37° C. and TEER was measured every hour using automated data collection. This overnight measurement of TEER before the experimental start allowed for determination of baseline TEER in each well and as a quality control of a stable electrical resistance.

Preparation of *Bifidobacterium Breve*

Two days prior to co-incubation with the Caco-2 cells *Bifidobacterium breve* DSM 32356 and *Bifidobacterium breve* DSM 20213 were cultured overnight anaerobically in Man Rogosa Sharp (MRS) broth (BD Difco 288110, UK) with 0.05% Cysteine hydrochloride (CyHCl) (Merck 102839, Germany). The day prior to co-incubation the grown cultures were reinoculated in MRS with 0.05% CyHCl (100 µL bacteria solution in 10 mL MRS with 0.05% CyHCl). A dilution row was generated by transferring 1 mL of mixed inoculated culture with 10 mL MRS with 0.05% CyHCl. This was repeated 5 times. The bifidobacteria were cultured anaerobically overnight at 37° C. On the day of co-incubation bacterial growth was evaluated by measuring $OD_{600\ nm}$ and cultures representing late exponential/early stationary phase were selected. For each strain 2 vials representing late exponential/early stationary phase were pooled and centrifuged at 3500×g for 10 min, in order to collect the bacteria pellet. The supernatants were discarded and 20 mL of 37° C. warm HBSS was added and the bacteria were washed and spun down at 3500×g for 10 min. This washing procedure was repeated once followed by a third washing step using 20 mL pre-heated Abx-free medium. Bacterial cells were harvested by spinning at 3500×g for 10 min and the supernatant was discarded. Bacterial cells were resuspended in 5 mL pre-heated Abx-free medium and $OD_{600\ nm}$ was adjusted to 3.8.

Stimulation of Caco-2 cells with *Bifidobacterium Breve*

In order to stimulate the Caco-2 cells with bifidobacteria, CellZscope measurements were paused, the CellZscope was removed from the $CO_2$ incubator and 100 µL of apical medium was removed from each transwell. A 100 µL of bacteria solution (final $OD_{600\ nm}$ of 0.5) or media control (MEM) was added to the relevant wells (each in triplicate).

The CellZscope were transferred back to the $CO_2$ incubator and the TEER measurements were resumed and continued overnight. Changes in TEER during bacterial stimulation were calculated relative to the latest value recorded immediately prior to the stimulation (baseline measurement, set to 100%). Area under the curve was calculated for each well and different bacterial stimulation were compared by one-way ANOVA including Tukey's multiple comparisons test.

Results

The ability to increase TEER in Caco-2 monolayers was tested for the following strains: *Bifidobacterium breve* DSM 32356 and *Bifidobacterium breve* DSM 20213 and compared to medium control (FIG. 2). *Bifidobacterium breve* DSM 32356 was found in vitro to enhance the TEER in the polarized monolayer of Caco-2 epithelial cells. *Bifidobacterium 5 breve* DSM 32356 significantly increased TEER area-under-the-curve (AUC) to a mean of 380 compared to the control group (medium only) that had a mean of 27, showing an increase in mean TEER AUC of 1311%. Also, *Bifidobacterium breve* DSM 20213 increased mean TEER AUC but only to mean value of 228. When comparing *Bifidobacterium breve* DSM 32356 to *Bifidobacterium breve* DSM 20213, *Bifidobacterium 10 breve* DSM 32356 had a significantly higher mean TEER value (44% higher).

Example 3

Measurement of IL-10/IL-12 Ratio

Preparation of *Bifidobacterium Breve*

*Bifidobacterium breve* DSM 32356 was inoculated and cultured anaerobically with AnaeroGen pads (Thermo Scientific AN0025A, UK) at 37° C. in pH 6.5 MRS (de Man, Rogosa and Sharpe broth, Difco, 288110, UK) with 0.05% Cysteine hydrochloride (CyHCl) (Merck 102839, Germany) overnight. A 10-fold dilution series was prepared from the overnight culture and incubated overnight anaerobically at 37° C. A stationary growth phase culture was selected based on measures of optical density at 600 nm (OD600). The bacterial culture was centrifuged for 2 min at 6000 g, washed twice in Hank's Balanced Salt Solution (HBSS, Gibco 14175), and resuspended in antibiotic-free cell culture media (RPMI 1640, Biological Industries, Kibbutz Beit-Haemek, Israel +10% Glycerol) at OD 0.05.

Monocyte-Derived Dendritic Cell (DC) Generation

Human peripheral blood mononuclear cells (PBMCs) were obtained from buffy coats of four healthy donors. Briefly, a density gradient cell separation was performed by centrifugation using Ficoll-Paque PLUS™ (GE Healthcare, Freiburg, Germany). Monocytes were isolated by positive selection for CD14 using magnetic-activated cell sorting with CD14 microbeads (Miltenyi Biotec, Bergisch Gladbach, Germany) and cultured at a density of $2 \times 10^6$ cells/mL in complete Dendritic cell (DC) media (RPMI 1640 supplemented with 10 mM HEPES (Sigma-Aldrich, Schnelldorf, Germany), 50 μM2-ME (Sigma-Aldrich, Schnelldorf, Germany), 2 mM L-glutamine (Life Technologies Ltd, Paisley, UK), 10% heat-inactivated fetal bovine serum (Invitrogen, Paisley, UK), 100 U/mL penicillin (Biological Industries, Kibbutz Beit-Haemek, Israel), and 100 μg/mL streptomycin (Biological Industries, Kibbutz Beit-Haemek, Israel) containing 30 ng/mL human recombinant IL-4 and 20 ng/mL human recombinant GM-CSF (both from Sigma-Aldrich, Saint Louis, Mo., USA) at 37° C., 5% $CO_2$. Fresh complete DC media containing full doses of IL-4 and GM-CSF was added after three days of culture. At day 6, differentiation to immature DCs was verified by surface marker expression analysis (CD11c>90% expression; CD1a>75% expression).

DC Stimulation

Immature DCs were resuspended in fresh complete DC media containing no antibiotics, seeded in 96-well plates at $1 \times 10^5$ cells/well, and allowed to acclimate at 37° C., 5% $CO_2$, for at least one hour before stimulation. DC were stimulated for 20 hours with 20 μL of *B. breve* (DSM 32356) bacterial culture in total OD=0.01 or DC medium (unstimulated control) at 37° C., 5% $CO_2$. After stimulation, DC supernatants were sterile filtered through a 0.2 μm Acro-Prep Advance 96-well filter plate (Pall Corporation, Ann Arbor, Mich., USA) for cytokine quantification.

Cytokine Quantification from DCS

Secreted levels of IL-10 and IL-12p70 were quantified using electrochemiluminescence assays (U-plex panel, Meso Scale Discovery, MSD, Rockville, Md., USA) according to the manufacturer's instructions. The mean of lower detection limit for IL-10 and IL-12p70 was 0.04015 and 0.214 pg/ml respectively.

Statistical Analysis

Statistical analysis was performed with GraphPad Prism 7 software (GraphPad Software, La Jolla, USA). Cytokine mean values were compared using Mann-Whitney test. Data are expressed as mean±SEM in pg/ml, or the ratio IL-12p70:IL-10. When a value was below detection limit of detection or below fitting curve, it was replaced by half-limit of detection.

Results

After 20 hours stimulation with *Bifidobacterium breve* DSM 32356, the supernatants of monocyte-derived dendritic cells were collected, and their cytokine profile was investigated.

Figure 3A:
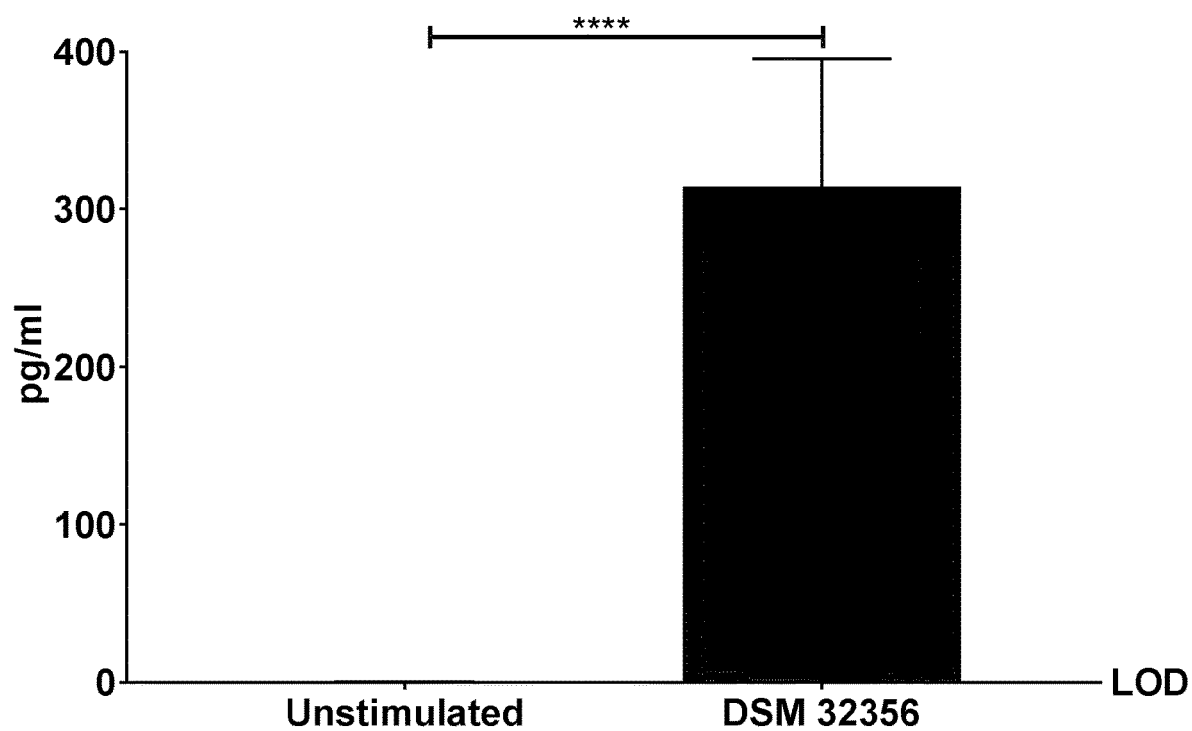
Figure 3B:
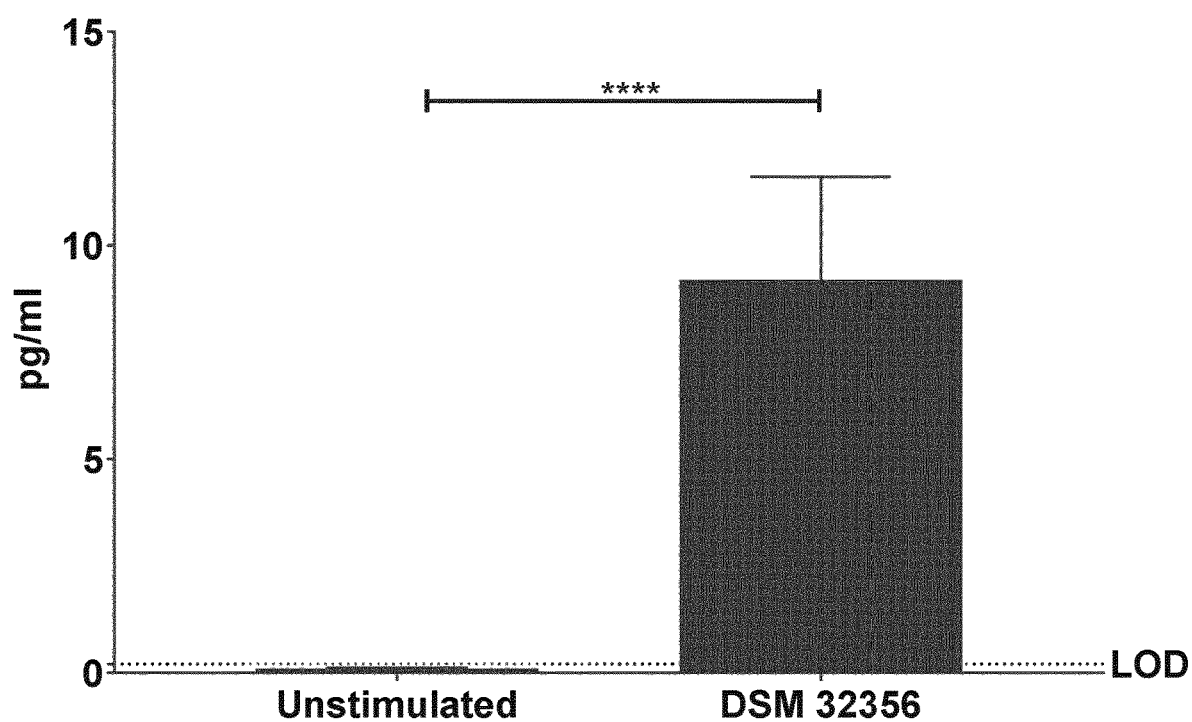
Figure 3C:
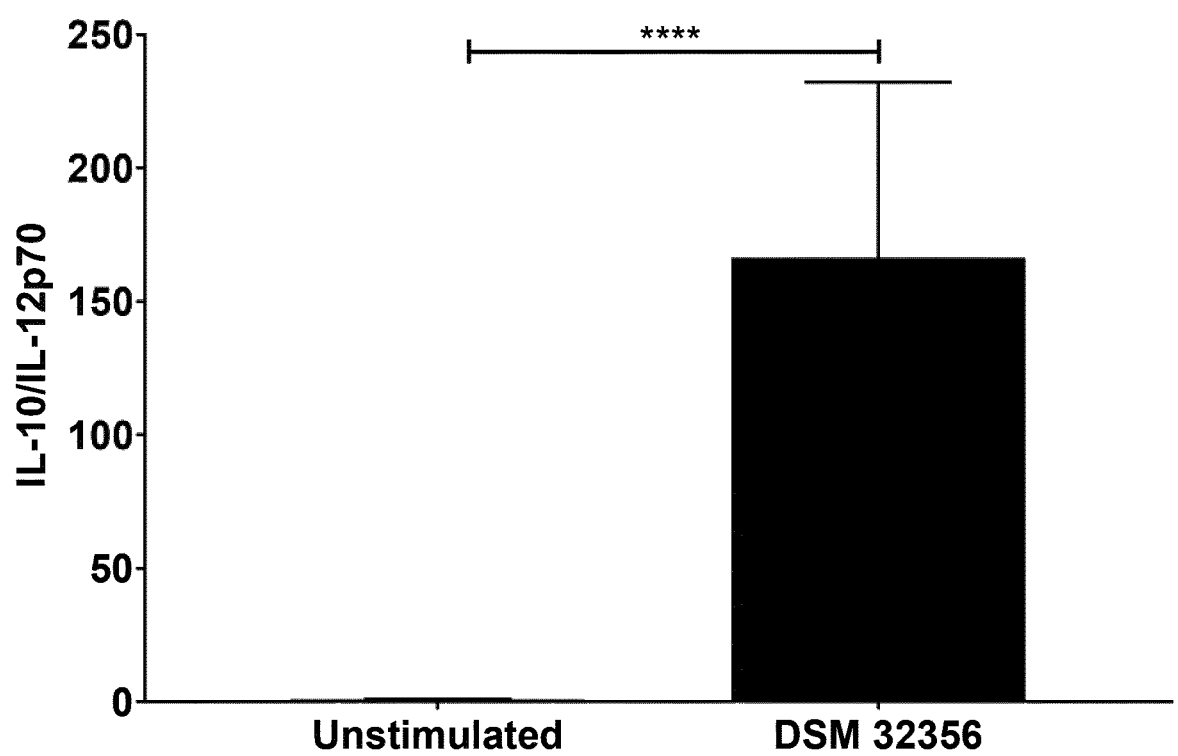

*Bifidobacterium breve* DSM 32356 was shown to activate immune responses from human monocyte derived DCs through the secretion of the T cell-stimulating cytokine IL-12p70 with a mean value of 9.19 pg/ml (FIG. 3B) and the anti-inflammatory IL-10 with a mean value of 313.9 pg/ml (FIG. 3A). Secretion of IL-10 from unstimulated DCs showed a mean value of 0.17 pg/ml, and IL-12p70 was out of detection limit. The IL-10:IL-12p70 ratio of unstimulated dendritic cells was 0.8:1, while it was increased to 166:1 in *Bifidobacterium breve* DSM 32356 stimulated dendritic cells (FIG. 3C).

Example 4

In Vivo Study of Protection of *Bifidobacterium breve* DSM 32356 Against Acetylsalicylic Acid Induced Damage of the Small Intestine Mucosa The present example demonstrates the ability of DSM 32356 to attenuate and/or reverse the effect of NSAID induced small intestinal damage. More specifically, the present trial has demonstrated the ability of DSM 32356 to attenuate and/or reverse low-dose, long-term acetylsalicylic acid (aspirin)-induced deterioration of small intestinal mucosa tissue as assessed by capsule endoscopy in healthy volunteers.

The trial was a single-site, randomised, double-blind, placebo-controlled, two-armed, parallel-group trial in healthy, adult volunteers. The trial investigated the effect of daily intake of the probiotic strain DSM 32356 or placebo when co-administered to daily intake of 300 mg of acetylsalicylic acid (aspirin).

The trial included a run-in period of two weeks duration followed by a six weeks intervention period where DSM 32356/placebo and acetylsalicylic acid (aspirin) was co-administered. After the 6 weeks, DSM 32356/placebo was given for two additional weeks to investigate the potential effects of DSM 32356 on intestinal healing after long-time acetylsalicylic acid (aspirin) use.

Subjects participated in the trial for a total duration of 10 weeks including the run-in phase. Besides the screening visit, the trial consisted of 6 visits during the 8-week intervention period.

After having given their written informed consent, subjects completed the screening procedures to evaluate their eligibility for participation in the trial and completed a run-in period of two weeks duration to washout possible pre-trial probiotics and/or use of medication. After baseline assessments at Visit 2, subjects started daily intake of 300 mg acetylsalicylic acid (aspirin) and were also randomly assigned to 8 weeks daily intake of active *Bifidobacterium breve* DSM 32356 or placebo product in a ratio of 1:1.

We aimed for 30 subjects to complete the trial in each arm, and assuming a moderate drop-out rate of subjects, we randomized a total of 75 subjects. The trial had in total 66 subjects completing the trial with available efficacy data (ITT population). Table 1 illustrates the subject disposition and Table 2 illustrates and compares the baseline characteristics of the active and placebo arm.

TABLE 1

Subject disposition during the trial. Data showed in this application is on the Intention to treat population (n = 66)

| | N |
|---|---|
| Subjects screened: | 109 |
| Subjects included in run-in phase | 75 |
| Subjects randomized | 75 |
| Subjects taking trial product | 75 |
| Subjects included in intention to treat population | 66 |

TABLE 2

Baseline characteristics and accountability of aspirin and trial product of both arms in the intention to treat population. Data is presented as mean ± SD.

| | ITT population | | |
|---|---|---|---|
| | DSM 32356 | Placebo | P-value |
| N | 35 | 31 | |
| Age (years) | 30.5 ± 6.8 | 31.2 ± 6.4 | 0.6675 |
| Gender (m/f) | 16/19 | 14/17 | 0.9641 |
| Ethnicity (non-Caucasians) | 2 | 0 | 0.4012 |
| Height (cm) | 172.2 ± 12.1 | 173.4 ± 10.2 | 0.6662 |
| Weight (kg) | 73.5 ± 12.5 | 72.0 ± 11.4 | 0.6137 |
| BMI | 24.6 ± 2.1 | 23.8 ± 2.2 | 0.1235 |
| Blood pressure, Systolic (mm hg) | 124.1 ± 7.8 | 121.6 ± 10.2 | 0.2756 |
| Blood pressure, Diastolic (mm hg) | 78.7 ± 6.9 | 77.1 ± 7.6 | 0.3801 |
| alcohol consumption ("drinks" per week) | 5.1 ± 3.2 | 5.5 ± 3.7 | 0.6919 |
| Accountability of aspirin (100% = product subj. should have taken) | 98.7 ± 2.4 | 99.1 ± 1.9 | |
| Accountability of trial product (100% = product subj. should have taken) | 98.6 ± 2.4 | 99.0 ± 1.9 | |

Criteria for Inclusion was:
Written informed consent
Healthy and without any gastrointestinal discomfort/pain symptoms
Age ≥18-≤40 years of both gender
Sedentary lifestyle (weekly training load below 2 hours within endurance sports)
Willing to abstain from any other probiotic products and/or medication known to alter gastrointestinal function throughout the participation of the trial Criteria for Exclusion was:
Abdominal surgery which, as judged by the investigator, might affect the GI function (except appendectomy and cholecystectomy)
History of peptic ulcer disease
Any known bleeding disorder
Allergy to aspirin
History of *H. pylori* disease
Resting diastolic blood pressure 90 mmHg
Resting systolic blood pressure 140 mmHg
A current diagnosis of psychiatric disease
Systemic use of antibiotics, steroids (except contraceptives) or antimicrobial medication in the last 2 months
BMI >27
Daily usage of non-steroidal anti-inflammatory drugs in the last 2 months or incidental use in the last 2 weeks prior to screening (Aspirin, Ibuprofen, Diclofenac, Naproxen, Celecoxib, Mefenamic acid, Etoricoxib, Indometacin)
Usage of medications, except contraceptives, in the last 2 weeks prior to screening
Diagnosed inflammatory gastrointestinal disease and/or irritable bowel syndrome
Lactose intolerance
Any other disease that, by the Investigators discretion, could interfere with the intestinal barrier function of the subject
Participation in other clinical trials in the past 2 months prior to screening
Regular use of probiotics in the last 2 months
Smoking and/or frequent use of other nicotine products
Desire and/or plans on changing current diet and/or exercise regime during the participation of this trial
Use of laxatives, anti-diarrheals, anti-cholinergics and PPI within last 2 months prior to screening
Use of immunosuppressant drugs within last 4 weeks prior to screening
For Women: Pregnancy or lactation.

The Primary endpoint was the effect of 8 weeks oral supplementation of DSM 32356 versus placebo on small intestinal mucosa damage when co-administered to a 6-week acetylsalicylic acid (aspirin challenge) measured as the area-under-the-curve of the capsule endoscopy Lewis score between Visit 2 (randomization) and Visit 7 (end of treatment).

The first of the ranked secondary endpoint was the effect of 8 weeks oral supplementation of DSM 32356 versus placebo on small intestinal mucosa damage when co-administered to a 6-week acetylsalicylic acid (aspirin) challenge measured as the area-under-the-curve for Visit 2-Visit 7 ulcer number from capsule endoscopy.

During the entire trial subjects were instructed to maintain their habitual life style with regards to diet, physical activity level and sleep habits.

Small intestine mucosa deterioration was evaluated using capsule endoscopy as well as indirect with biomarkers in feces and blood samples drawn at visit 2-7.

Intake of probiotic products as well as food and food supplements containing probiotics were not allowed from the screening visit and until the end of the intervention period.

Subjects were not withdrawn from the trial due to single violations, but violations were recorded as protocol deviations.

Any use of illicit drugs (euphorics or stimulants, such as *cannabis*, opium) was prohibited during the trial.

Subjects were asked to:

Refrain from consuming and food products that may contain live microbes (i.e. fermented milk products)

Refrain from taking any non-steroidal anti-inflammatory drugs (NSAIDs) during the trial period Refrain from participating in other clinical trials Refrain from consuming alcohol for two days prior to Visit 2-7

Refrain from consuming spicy food two days prior to Visit 2-7

Refrain from consuming caffeine two days prior to Visit 2-7

Avoid strenuous exercise two days prior Visit 2-7

Fast overnight from (10:00) before attending the Visit 2-7. Clear liquids such as water, soft drinks, de-caffeinated tea/coffee were allowed up until midnight the day before a visit.

Capsule endoscopy is useful to detect small intestine inflammation and damage in the form of villous oedemas, ulcers and stenosis. The capsule endoscopy method was used during visit 2-7 using the Pillcam capsule from Medtronic.

The subjects were asked to fast from 10:00 the day before the visit in order to empty the intestine before the capsule endoscopy procedure. Subjects met fasting in the morning of the visit. The Pillcam signal receiver belt was connected to the subject's upper body before the Pillcam capsule was swallowed with a glass of water. The Pillcam capsule then travels through the ventricle and small intestine and sends data in the form of pictures to the receiver. Data from the capsule was captured for a total of 8 hours after which the capsule is expected to have passed the small intestine. The subjects were allowed to leave the site during the 8-hour capsule recording but were advised not to be physically active during these 8 hours. After 4 hours, subjects were allowed to have a light meal.

In total 5 well-trained gastroenterologists were involved in reviewing and scoring the video data from the capsules. The damage observed in the small intestine from the capsule were divided in the three categories: Villous oedemas, ulcers and stenosis. These three categories were rated both separately and for the primary endpoint also combined into one score, the Lewis Score (Gralnek et al., 2008) (Gralnek I M, Defranchis R, Seidman E, Leighton J A, Legnani P, Lewis B S. Development of a capsule endoscopy scoring index for small bowel mucosal inflammatory change. Aliment Pharmacol Ther. 2008; 27(2):146-154. doi:10.1111/j.1365-2036.2007.03556.x), which is a well-recognized clinical and scientific score for intestinal damage.

The following rules were applied for assessments of data from the capsules:

Safety:

Within a week from the capsule visit, at least one capsule reviewer confirmed that the capsule had passed the small intestine (by verifying from the last pictures that the capsule is in the colon).

Data Quality:

A randomization system was created, so that in parallel to being randomized to *Bifidobacterium breve* DSM 32356/placebo treatment, subjects were also randomized to 2 of the 5 reviewers to oversee the capsule data from that subject.

The two reviewers that were appointed by the randomization system reviewed all capsule data from all capsule visits for that subject. The two reviewers overseeing capsule data from a subject were also blinded from each other and not being allowed to communicate to each other in any way regarding the capsule data.

Mean capsule data values for those 2 reviewers were calculated. In cases that the data from the two reviewers differed with 4 or more number of ulcers, a third reviewer (the principal investigator) also reviewed the Pillcam dataset for that visit and a mean value of all 3 reviewers were calculated and used as the final data point for that visit.

The results are provided in the figures showing data from the ITT population.

As the results show, the trial met its primary and first secondary endpoint, showing a clear and statistically significant protective effect of the DSM 32356 strain against aspirin-induced intestinal damage as observed on the Lewis score (FIG. 5), and total number of ulcers (FIG. 6).

Example 5

Quantification of Prostaglandin E2 and Thromboxane B2 Concentrations in Blood Samples Methods As exploratory endpoints, post-hoc intervention effects on prostaglandin E2 (PGE2) and thromboxane B2 (TBX2) in serum samples downstream of cyclooxygenase (COX) were studied.

After unblinding, a post-hoc lab analysis was performed on 2 biolipids PGE2 and TXB2 downstream from the COX enzyme in fasting serum samples obtained during visit 2 to visit 7. The extraction protocol and LC-MS/MS analysis were performed by Ambiotis SAS (France) as described previously (Le Faouder et al. 2013) Le Faouder, P. et al. LC-MS/MS method for rapid and concomitant quantification of pro-inflammatory and pro-resolving polyunsaturated fatty acid metabolites. *J. Chromatogr. B* 932, 123-133 (2013). Ambiotis were kept blinded for intervention during analyses and analyses were performed in single measurements.

Results

Intake of acetylsalicylic acid (aspirin) was associated with robust inhibition of serum PGE2 and TXB2 concentrations (FIG. 7). *Bifidobacterium breve* DSM 32356 intervention did not alter these well-described acetylsalicylic acid-induced changes in metabolites downstream of COX. This suggests that the protective actions of *Bifidobacterium breve* DSM 32356 do not interfere with the specific cardiovascular-protective properties of acetylsalicylic acid.

Example 6

Systemic Cytokine Profiling

Methods

Cytokine Quantification from Heparin Plasma

Heparin plasma samples from visit 2 to 7 from 31 subjects from the placebo group, and from the active group (consumers of *B. breve*, DSM 32356) were collected to analyze their cytokine profiles. Secreted levels of IFN-γ, IL-10, IL-12p70, IL-13, IL-1β, IL-2, IL-4, IL-6, IL-8 and TNF-α were quantified using the V-plex human proinflammatory panel 1 from Meso Scale Discovery (Cat. #K15049D) according to the manufacturer's protocol. C-Reactive Protein (CRP) levels were also quantified using a V-plex single assay (Cat. #K151STD) according to the manufacturer's instructions. Inter-plate variation was assessed using a bridge control sample.

Statistical Analysis

Statistical analysis was performed with GraphPad Prism 7 software (GraphPad Software, La Jolla, USA). Cytokine values were compared using a 2-way ANOVA with Sidak's comparison. Data are expressed as median +95% CI in mg/L for CRP and pg/ml for the rest of the cytokines. When a value was below the limit of detection or below fitting curve, it was replaced by half-lower limit of detection (LOD).

Results

No significant differences were found between the placebo and active groups in any of the measured cytokines or CRP. Therefore, consumption of *B. breve* (DSM 32356) did not induce a systemic immune-response. All the measurements of IFN-γ, IL-10, IL-6, IL-8, TNF-α and CRP were within detection range, and their inter-plate variation values were below 20% (See table 3 and FIGS. 8 to 13). As for IL-12p70, IL-13, IL-1β, IL-2 and IL-4 more than 31.9% of the measurements were below detection limits, which increased inter-plate variation (See table 3).

Table 3. Mean of lower detection limits for the analyzed cytokines, Inter-plate variation based on CV values of the bridge control sample and % of samples below detection limit. * samples for IL-13 measurements were 26 for the placebo and 28 for the active group.

TABLE 3

| Assay | Mean LOD (pg/ml) | Inter-plate variation Bridge control CV | % samples below detection limit |
|---|---|---|---|
| IFN-γ | 0.259 | 13.1 | 0 |
| IL-10 | 0.016 | 12.5 | 0 |
| IL-12p70 | 0.036 | 25.2 | 31.9 |
| IL-13 | 0.146 | 33.9 | * 77 |
| IL-1β | 0.022 | 58 | 68.5 |
| IL-2 | 0.036 | 63.2 | 63.2 |
| IL-4 | 0.008 | 47.1 | 76.4 |
| IL-6 | 0.031 | 8.4 | 0 |
| IL-8 | 0.119 | 4.8 | 0 |
| TNF-α | 0.055 | 10.2 | 0 |
| CRP | 1.301 | 17.5 | 0 |

Example 7

*Bifidobacterium breve* Recovery and Microbiota Composition of Stool Samples

As exploratory endpoints, post-hoc intervention effects on *Bifidobacterium breve* abundancy and microbiota composition in stool samples were studied.

After unblinding, a post-hoc lab and bioinformatic analysis was performed on DNA extracted from all obtained fecal samples using a NucleoSpin 96 Soil kit (Macherey-Nagel) and randomly sheared into 350 bp fragments. Libraries were constructed using NEBNext Ultra Library Prep Kit for Illumina (New England Biolabs) and sequenced to at least 30 million read pairs per sample (2×150 bp paired-end Illumina sequencing). Sequencing reads were filtered to remove human and low-quality reads, mapped to the Clinical Microbiomics Human Gut 22M gene catalog, and summarised as a taxonomic relative abundance table as described previously (Nielsen et al. 2014) Nielsen, H. B. et al. Identification and assembly of genomes and genetic elements in complex metagenomic samples without using reference genomes. *Nat. Biotechnol.* 32, 822-828 (2014). The involved parties were kept blinded for intervention during analyses. Changes in relative abundances of taxa between visit 2 and the integral of later time-points was tested using Wilcoxon rank sum test and corrected for multiple comparison using a Bonferroni correction. Similarly, the Bray-Curtis distance between visit 2 and later time-points were compared between the two arms (t-test).

Results

DNA sequencing of all fecal samples obtained showed a clear increase in abundance after randomisation of *Bifidobacterium breve* in fecal samples obtained from subjects in the *Bifidobacterium breve* DSM 32356 arm compared to the placebo arm confirming study product compliance (FIG. 14).

Intervention with *Bifidobacterium breve* DSM 32356 was not associated with significant changes in abundance of specific microbial taxa nor in the changes of the overall microbiome composition as revealed by Bray-Curtis dissimilarity index (FIG. 15).

Example 8

The overall aim with this experiment was to explore if *Bifidobacterium breve* DSM 32356 influenced the degradation of aspirin in vitro.

Assumptions

In the clinical trial each subject was dosed 300 mg aspirin (acetylsalicylic acid) per day. It is assumed that the dose was taken with approximately 1 dL of water which would correspond to 0.3 g/0.1 L=3 g/L. The molecular weight of aspirin is 180.157 g/mol. Assumed maximal exposure in the gut would then be (3 g/L)/(180.157 g/mol)=0.01665 mol/L=16.65 mM.

To cover a wide concentration range of acetylsalicylic acid the following concentrations were used: 20, 10, 5, 2.5, 1.25, 0.625, 0.3125 and 0 mM of acetylsalicylic acid.

Preparation of *Bifidobacterium breve*

Two days prior to incubation with the acetylsalicylic acid *Bifidobacterium breve* DSM 32356 was cultured overnight anaerobically in Man Rogosa Sharp (MRS) broth (BD Difco 288110, UK) with 0.05% cysteine hydrochloride (CyHCl) (Merck 102839, Germany). The next day the grown culture was reinoculated in fresh MRS with 0.05% CyHCl (100 µL bacteria suspension in 10 mL MRS with 0.05% CyHCl). Six dilution rows were generated by transferring 1 mL of mixed inoculated culture to 10 mL MRS with 0.05% CyHCl. This was repeated 5 times. The bifidobacteria were cultured anaerobically overnight at 37° C. On the day of incubation with acetylsalicyl acid bacterial growth was evaluated by measuring optical density at 600 nm ($OD_{600\,nm}$) and cultures representing late exponential/early stationary phase were selected. For every 2 dilution rows, the 2 vials representing late exponential/early stationary phase were pooled (adding up to 3 vials in total) and together with a medium control vial the tubes were centrifuged at 3500×g for 5 min, in order to collect the bacteria pellet. The supernatants were discarded and 35 mL of MRS with 0.05% CyHCl was added and the bacteria were washed and spun down at 3500×g for 5 min. The washing procedure was repeated once. Further, 15 mL of MRS with 0.05% was added to each for the 3 vials with bacteria pellets. After resuspending the pellets, the 3×15 mL bacteria suspensions were pooled in 1 tube and spun down at 3500×g for 10 min and the supernatant was discarded. A total of 20 mL MRS with 0.05% CyHCl was added and the bacteria was resuspended. $OD_{600\,nm}$ was adjusted to 12 corresponding to a bacterial density of approximately 4.25× $10^9$ CFU/mL.

Preparation of Acetylsalicylic Acid Solutions

Acetylsalicylic acid, Sigma, A6810, 400 mg was weighed out and dissolved in 100 mL of MRS with 0.05% CyHCl. pH was adjusted to the pH of the media control (pH=6) using 2M NaOH (Diluted from 27% sodium hydroxide solution, Merck). The aspirin solution was diluted 2-fold 6 times in MRS with 0.05% CyHCl to obtain the following concentrations of aspirin 22.2, 11.1, 5.6, 2.8, 1.39, 0.69 and 0.35 mM. All solutions, including a medium control of MRS with 0.05% CyHCl, were sterile filtered.

Incubation of Bifidobacterium breve DSM 32356 with Aspirin

Nine mL of each acetylsalicylic acid solution (22.2, 11.1, 5.6, 2.8, 1.39, 0.69 and 0.35 mM) and the control condition (0 mM) were added to different sterile tubes in duplicate. To one of the dilution rows 1 mL of DSM 32356 suspension was added to each tube to achieve a final concentration of 20, 10, 5, 2.5, 1.25, 0.625, 0.3125 and 0 mM of acetylsalicylic acid and $4.25 \times 10^8$ CFU/mL of bacteria. To the second dilution row 1 mL of MRS with 0.05% CyHCl was added and pH was adjusted to 4.5 using approximately 30 µL of HCl (sodium chloride, VWR Chemicals) per tube. Both dilution rows were incubated anaerobically for 24 hrs at 37° C. After incubation, pH was measured in each vial and the solutions were sterile filtered and frozen at −80° C. until metabolite analysis.

Metabolite Analysis

All samples were diluted 10 times in 10 mM ammonium formate (LC-MS grade from VWR Chemicals) with 0.1% formic acid (LC-MS grade from VWR Chemicals). In order to ensure proper quantification of acetylsalicylic acid and salicylic acid, samples A6 and B6 were additionally diluted 2 times, samples A7 and B7 were additionally diluted 4 times and samples A8 and B8 were additionally diluted 10 times.

For quality control, a mixed pooled sample (QC sample) was created by taking a small aliquot from all samples. This QC sample was analysed with regular intervals throughout the sequence.

The analysis was carried out using a UPLC system (Vanquish, Thermo Fischer Scientific) coupled with a high-resolution quadrupole-orbitrap mass spectrometer (Q Exactive™ HF Hybrid Quadrupole-Orbitrap, Thermo Fischer Scientific). An electrospray ionization interface was used as ionization source. Analysis was performed in negative and positive ionization mode. The QC sample was analysed in MS/MS mode for identification of compounds. The UPLC was performed using a slightly modified version of the protocol described by Doneanu et al. 2011 (Doneanu, C. E., Chen, W. & Masseo, J. R. (2011) Waters Application note, 720004042en).

Data was processed using Compound Discoverer 3.0 (Thermo Fischer Scientific). Compound extraction was performed by extracting all features from the raw data followed by a feature detection by grouping features belonging to the same compound. Isotope patterns together with the accurate mass were used to determine the molecular formula. Identification of compounds were performed by one of 3 levels of annotation:

1) Confident identification by accurate mass, MS/MS spectra and known retention time identified via standards.

2) Annotation was based on two pieces of information and was divided into two sublevels: a) based on accurate mass and known retention time as obtained from standards analysed on the same system, b) based on accurate mass and MS/MS spectra from an external library.

3) Annotations on this level was based on library searches using the accurate mass and elemental composition alone. The library searches were performed with an acceptable mass deviation of +/−3 ppm.

Compounds related to the amount of aspirin added were found by calculating the correlation coefficient between peak areas obtained and the acetylsalicylic acid concentration. The behavior of compounds with correlation coefficients higher than 0.9 were analysed in more detail to investigate if they could be acetylsalicylic acid derivatized metabolites.

Results

All the pH adjusted samples (B1-B8) had a similar pH before and after 24 hours of incubation, whereas the samples inoculated with Bifidobacterium breve DSM 32356 all had a pH of 6 prior to incubation and pH of 4-4.5 after incubation (see Table 4).

TABLE 4

| Final acetylsalicylic acid conc | Sample id | Inoculation (~4.25 × $10^8$CFU/ml) | pH before incubation | pH after 24 hrs of incubation |
| --- | --- | --- | --- | --- |
| 0 | A1 | + | 6 | 4 |
| 0.3125 | A2 | + | 6 | 4 |
| 0.625 | A3 | + | 6 | 4 |
| 1.25 | A4 | + | 6 | 4 |
| 2.5 | A5 | + | 6 | 4 |
| 5 | A6 | + | 6 | 4 |
| 10 | A7 | + | 6 | 4-4.5 |
| 20 | A8 | + | 6 | 4-4.5 |
| 0 | B1 | − | 4.5 | 4.5 |
| 0.3125 | B2 | − | 4.5 | 4.5 |
| 0.625 | B3 | − | 4.5 | 4.5 |
| 1.25 | B4 | − | 4.5 | 4.5 |
| 2.5 | B5 | − | 4.5 | 4.5 |
| 5 | B6 | − | 4.5 | 4.5 |
| 10 | B7 | − | 4.5 | 4.5 |
| 20 | B8 | − | 4.5 | 4.5 |

Figure 16:
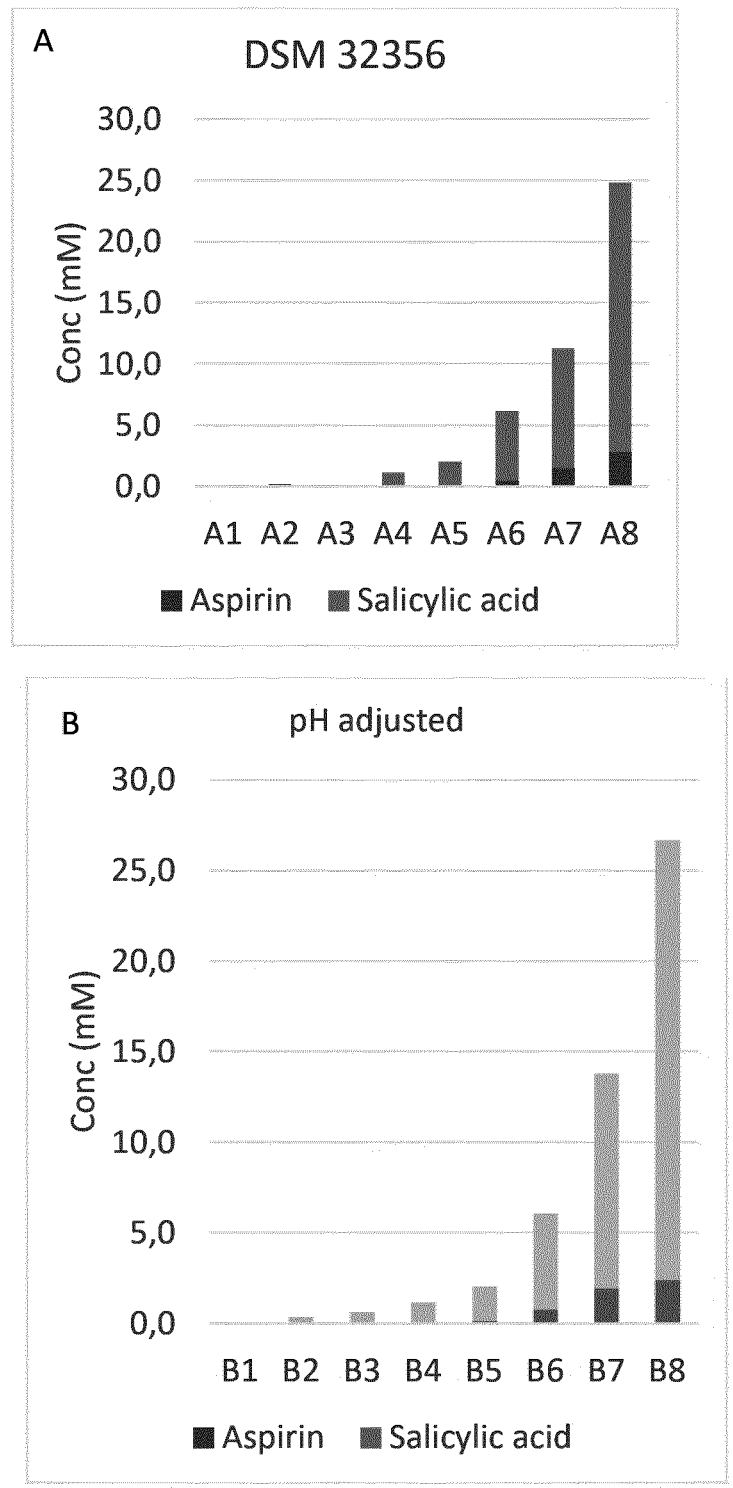

In all samples containing acetylsalicylic acid most of the acetylsalicylic acid was converted to salicylic acid after 24 hours of incubation with either Bifidobacterium breve DSM 32356 or after being acid-adjusted. When comparing the inoculated dilution row with the acid-adjusted dilution row no major differences were observed between the concentrations of acetylsalicylic acid and salicylic acid in the two sets of samples (FIG. 16).

Importantly, the concentrations of aspirin and salicylic acid, the two active compounds responsible for the therapeutic effects of aspirin, were not different between the inoculated and the acid adjusted dilution rows. When comparing added acetylsalicylic acid to detected peak areas several compounds seem to correlate and have increased peak areas when more acetylsalicylic acid was present. However, in the inoculated samples the bacteria seem to consume a number of compounds present in the media, an ability which is inhibited when increasing concentrations of aspirin are added due to inhibited bacterial growth. This inhibited growth is probably the underlying cause of the observed correlations, supported by the fact that these compounds are present in the same amount in the samples with high aspirin in the A sample set as in the B sample set. In conclusion, Bifidobacterium breve DSM 32356 does not appear to degrade acetylsalicylic acid.

The invention claimed is:

1. A method of supporting defense against intestinal tissue damage in a subject in need thereof, comprising orally administering to the subject a therapeutically effective amount of bacteria of Bifidobacterium breve strain DSM 32356 deposited at DSMZ-Deutsche Sammlung von Mikroorganismen and Zellkulturen GmbH (DSMZ) under accession number DSM 32356.

2. The method of claim 1, wherein the bacteria of strain DSM 32356 are administered in a composition that further comprises a cryoprotectant.

3. The method of claim 1, wherein the bacteria of strain DSM 32356 are administered in composition having a concentration of *Bifidobacterium breve* strain DSM 32356 of at least $10^6$ CFU/g.

4. The method of claim 1, wherein the bacteria of strain DSM 32356 are administered in a composition that further comprises bacteria of at least one other bacterial strain.

5. The method of claim 1, wherein the bacteria of strain DSM 32356 are administered in a composition that further comprises *Bifidobacterium infantis* bacteria.

6. The method of claim 5, wherein the bacteria of strain DSM 32356 are administered in composition having a total concentration of *Bifidobacterium breve* strain DSM 32356 and *Bifidobacterium infantis* bacteria of at least $10^6$ CFU/g.

7. The method of claim 1, wherein the bacteria of strain DSM 32356 are administered in a composition that further comprises one or more compounds selected from vitamins, prebiotics, fiber, fructo-oligosaccharides (FOS), galacto-oligosaccharides (GOS), and human milk oligosaccharides (HMO).

8. The method of claim 1, wherein the bacteria of strain DSM 32356 are administered in a composition that comprises *Bifidobacterium breve* strain DSM 32356 as the only probiotic component.

9. The method of claim 1, wherein the *Bifidobacterium breve* strain DSM 32356 is administered in an amount from $10^8$-$10^{11}$ CFU/day.

10. The method of claim 1, wherein the subject is undergoing NSAID administration of a non-steroidal anti-inflammatory (NSAID) drug.

11. The method of claim 10, wherein the subject is undergoing acetylsalicylic acid (aspirin) administration.

12. The method of claim 10, wherein the method is effective to reduce intestinal mucosal breaks or lesions as compared to a subject undergoing NSAID administration without administration of *Bifidobacterium breve* strain DSM 32356.

13. A composition comprising bacteria of *Bifidobacterium breve* strain DSM 32356 in dried, frozen, or freeze-dried form, further comprising an effective amount of a cryoprotectant.

14. The composition of claim 13, wherein the concentration of *Bifidobacterium breve* strain DSM 32356 in the composition is at least $10^6$ CFU/g.

15. The composition of claim 13, further comprising *Bifidobacterium infantis* bacteria.

16. The composition of claim 13, further comprising one or more compounds selected from vitamins, prebiotics, fiber, fructo-oligosaccharides (FOS), galacto-oligosaccharides (GOS), and human milk oligosaccharides (HMO).

17. The composition of claim 13, formulated for oral administration.

18. A feed or food product, dietary supplement, or pharmaceutical composition comprising *Bifidobacterium breve* strain DSM 32356 at an amount of at least $10^6$ CFU/g and an effective amount of a cryoprotectant.

19. A method for producing a feed or food product, dietary supplement, or pharmaceutical composition, comprising adding *Bifidobacterium breve* strain DSM 32356 to the feed, food product, dietary supplement, or pharmaceutical composition in a concentration an amount of at least $10^6$ CFU/g.

* * * * *

UNITED STATES PATENT AND TRADEMARK OFFICE
CERTIFICATE OF CORRECTION

PATENT NO. : 11,653,689 B2
APPLICATION NO. : 17/051653
DATED : May 23, 2023
INVENTOR(S) : Brynjulf Mortensen et al.

It is certified that error appears in the above-identified patent and that said Letters Patent is hereby corrected as shown below:

On the Title Page

Item (30) (Foreign Application Priority Data)
The European priority application number is changed from:
"8170250"
To the following:
--18170250.7--

Signed and Sealed this
Eleventh Day of June, 2024

Katherine Kelly Vidal
Director of the United States Patent and Trademark Office